US012019056B2

(12) United States Patent
Chen et al.

(10) Patent No.: US 12,019,056 B2
(45) Date of Patent: Jun. 25, 2024

(54) DIAGNOSIS OF TUBERCULOSIS AND OTHER DISEASES USING EXHALED BREATH

(71) Applicant: Zeteo Tech, Inc., Sykesville, MD (US)

(72) Inventors: Dapeng Chen, Sykesville, MD (US); Wayne A. Bryden, Sykesville, MD (US); Michael McLoughlin, Sykesville, MD (US)

(73) Assignee: Zeteo Tech, Inc., Sykesville, MD (US)

( * ) Notice: Subject to any disclaimer, the term of this patent is extended or adjusted under 35 U.S.C. 154(b) by 399 days.

(21) Appl. No.: 17/499,848

(22) Filed: Oct. 12, 2021

(65) Prior Publication Data

US 2022/0034854 A1 Feb. 3, 2022

Related U.S. Application Data

(63) Continuation-in-part of application No. PCT/US2020/048040, filed on Aug. 26, 2020.
(Continued)

(51) Int. Cl.
*G01N 33/497* (2006.01)
*A61B 5/08* (2006.01)
(Continued)

(52) U.S. Cl.
CPC ......... *G01N 30/7206* (2013.01); *A61B 5/082* (2013.01); *A61B 5/091* (2013.01); *A61B 5/097* (2013.01); *A61B 10/0045* (2013.01); *G01N 33/497* (2013.01); *A61B 5/087* (2013.01); *A61B 2010/0087* (2013.01); *A61B 2562/029* (2013.01); *G01N 2030/025* (2013.01); *G01N 2800/12* (2013.01)

(58) Field of Classification Search
CPC .............. G01N 33/497; G01N 30/7206; A61B 5/087; A61B 5/097; A61B 5/082
See application file for complete search history.

(56) References Cited

U.S. PATENT DOCUMENTS 6,062,392 A 5/2000 Birmingham
6,267,016 B1 7/2001 Call
(Continued)

FOREIGN PATENT DOCUMENTS

EP 3336543 A1 6/2018
EP 2823300 B1 10/2019
(Continued)

OTHER PUBLICATIONS

International Search Report and Written Opinion of ISA/KIPO for PCT/US2022/046393 dated Feb. 7, 2023.
(Continued)

*Primary Examiner* — Jamel E Williams
(74) *Attorney, Agent, or Firm* — Paradice & Li LLP; Anand S. Chellappa

(57) ABSTRACT

Disclosed are methods and devices for analyzing aerosol particles in exhaled breath using diagnostic tools that enable rapid, low cost and autonomous point of care assays for several diseases including respiratory tract diseases. Disclosed are methods and devices for capturing exhaled breath aerosols in a packed bed column and analyzing exhaled captured breath aerosols for tuberculosis diagnosis.

27 Claims, 16 Drawing Sheets

Related U.S. Application Data

Figure 1:
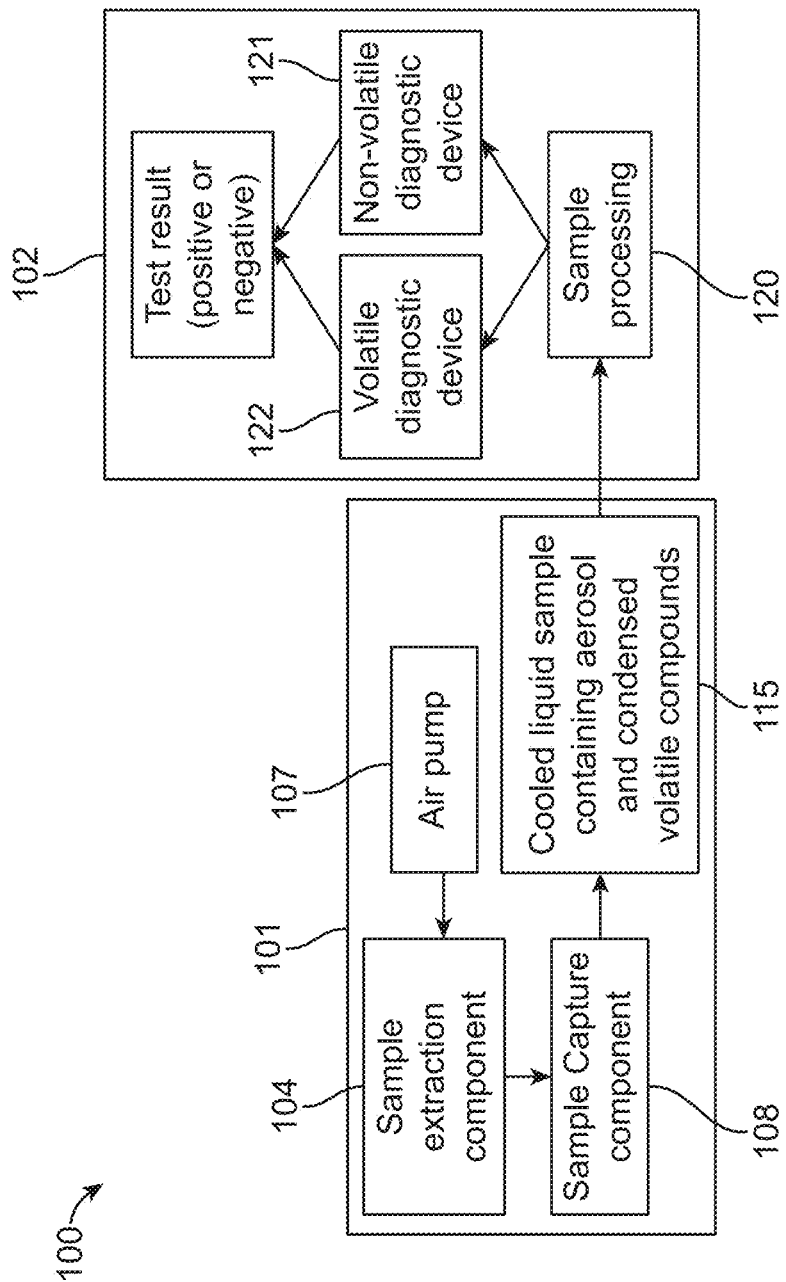

(60) Provisional application No. 63/069,120, filed on Aug. 23, 2020, provisional application No. 62/891,954, filed on Aug. 26, 2019.

(51) Int. Cl.

| | | |
|---|---|---|
| *A61B 5/091* | (2006.01) | |
| *A61B 5/097* | (2006.01) | |
| *A61B 10/00* | (2006.01) | |
| *G01N 30/72* | (2006.01) | |
| *A61B 5/087* | (2006.01) | |
| *G01N 30/02* | (2006.01) | |

(56) References Cited

U.S. PATENT DOCUMENTS

| | | | | |
|---|---|---|---|---|
| 8,409,870 | B2 | 4/2013 | Wuijckhuijse | |
| 2005/0137491 | A1* | 6/2005 | Paz | A61B 5/0878 |
| | | | | 600/543 |
| 2007/0068811 | A1 | 3/2007 | Tsukashima et al. | |
| 2008/0038207 | A1 | 2/2008 | Edwards et al. | |
| 2012/0172679 | A1 | 7/2012 | Logan et al. | |
| 2013/0217029 | A1 | 8/2013 | Sislian et al. | |
| 2016/0020080 | A1* | 1/2016 | Pyun | H01J 49/164 |
| | | | | 427/255.6 |
| 2016/0022946 | A1 | 1/2016 | Sislian et al. | |
| 2017/0303822 | A1 | 10/2017 | Allsworth et al. | |
| 2018/0246120 | A1 | 8/2018 | Bryden | |
| 2019/0000351 | A1* | 1/2019 | Scampoli | A61B 5/0836 |
| 2019/0282124 | A1 | 9/2019 | Wu et al. | |
| 2020/0345266 | A1 | 11/2020 | Schleich | |
| 2021/0345956 | A1 | 11/2021 | Keays et al. | |
| 2022/0034854 | A1* | 2/2022 | Chen | A61B 5/082 |
| 2022/0323045 | A1 | 10/2022 | Chen et al. | |
| 2023/0157573 | A1 | 5/2023 | Chen et al. | |

FOREIGN PATENT DOCUMENTS

| | | |
|---|---|---|
| JP | 09126958 A | 5/1997 |
| JP | 5848608 | 11/2017 |
| KR | 20100084528 A | 7/2010 |
| KR | 1020160130229 | 11/2016 |
| WO | 2004090534 A1 | 10/2004 |
| WO | 2009045163 | 4/2009 |
| WO | 2017197386 | 11/2017 |
| WO | 2019011750 A1 | 1/2019 |
| WO | 2019145678 A1 | 8/2019 |
| WO | 2021041571 A1 | 3/2021 |
| WO | 2021061330 | 4/2021 |
| WO | 2021201905 | 10/2021 |

OTHER PUBLICATIONS

B. Bake, P. Larsson, G. Ljungkvist, E. Ljungström, and A-C Olin, "Exhaled particles and small airways," Respiratory Research (2019) 20:8.

Fennelly K.P., Martyny J.W., Fulton K.E., Orme I.M., Cave D.M., et al. (2004) Cough-generated aerosols of *Mycobacterium tuberculosis*: a new method to study infectiousness. Am J Respir Crit Care Med 169: 604-609.

Dina Hashoul and Hossam Haick, "Sensors for detecting pulmonary diseases from exhaled breath," Eur. Respir. Rev. 2019; 28: 190011.

Hunt, J., "Exhaled breath condensate: An evolving tool for noninvasive evaluation of lung disease," J. Allergy Clin. Immunol. 2002; 110:28-34.

Maria D. King, Andrew R. McFarland, "Bioaerosol Sampling with a Wetted Wall Cyclone: Cell Culturability and DNA Integrity of *Escherichia coli* Bacteria," Aerosol Sci. Technol., 46:82-93, 2012.

James J. McDevitt, Petros Koutrakis, Stephen T. Ferguson, Jack M. Wolfson, M. Patricia Fabian, Marco Martins, Jovan Pantelic, and Donald K. Milton, "Development and Performance Evaluation of an Exhaled-Breath Bioaerosol Collector for Influenza Virus," Aerosol Sci. Technol. Jan. 1, 2013; 47(4): 444-451.

Benjamin Patterson, Carl Morrow, Vinayak Singh, Atica Moosa, Melitta Gqada, Jeremy Woodward, Valerie Mizrahi, Wayne Bryden, Charles Call, Shwetak Patel, Digby Warner, Robin Wood, "Detection of *Mycobacterium tuberculosis* bacilli in bio-aerosols from untreated TB patients," Gates Open Research 2018, 1:11.

Wood R., Morrow C., Barry C.E., III, Bryden W.A., Call C.J., Hickey A.J., et al.: Real-Time Investigation of Tuberculosis Transmission: Developing the Respiratory Aerosol Sampling Chamber (RASC). PLoS One. 2016; 11(1): e0146658.

Rachel C. Wood, Angelique K. Luabeya, Kris M. Weigel, Alicia K. Wilbur, Lisa Jones-Engel, Mark Hatherill, and Gerard A. Cangelosi, "Detection of *Mycobacterium tuberculosis* DNA on the oral mucosa of tuberculosis patients," Sci. Rep. 5, 8668 (2015).

Fatima B. Wurie, Stephen D. Lawn, Helen Booth, Pam Sonnenberg, Andrew C. Hayward, "Bioaerosol production by patients with tuberculosis during normal tidal breathing: implications for transmission risk," Thorax 2016; 71: 549-554.

Written Opinion of ISA/KIPO for PCT/US2020/048040 dated Dec. 9, 2020.

International Search Report and Written Opinion of ISA/KIPO for PCT/US2023/029760 dated Nov. 24, 2023.

* cited by examiner

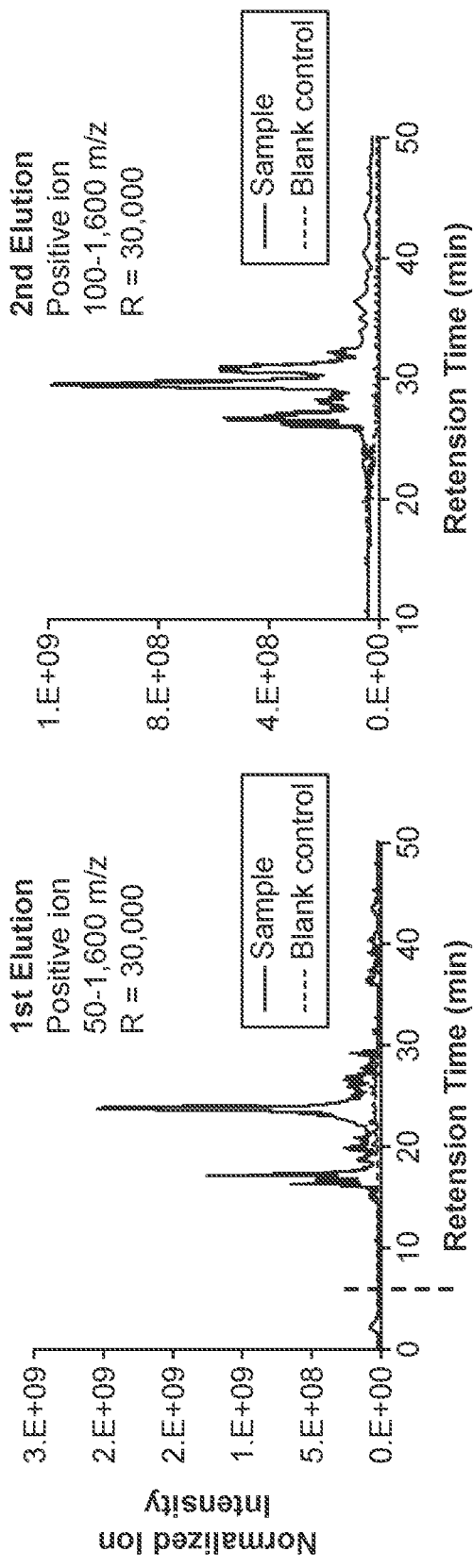
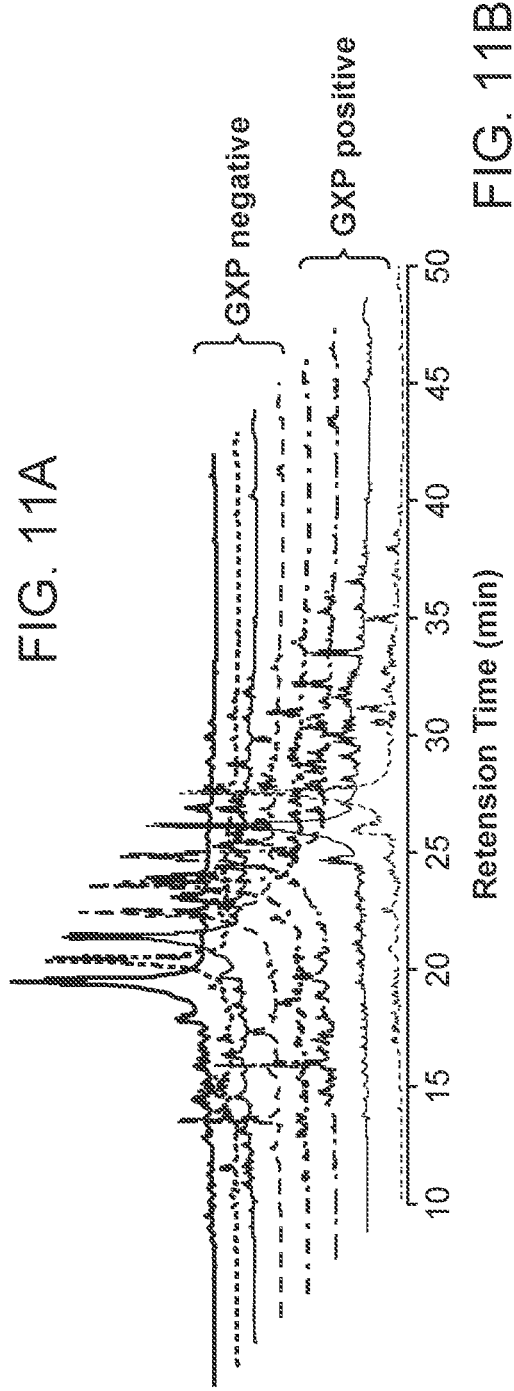
FIG. 11A
FIG. 11B

DIAGNOSIS OF TUBERCULOSIS AND OTHER DISEASES USING EXHALED BREATH

RELATED APPLICATIONS

This application is a continuation-in-part of International Application No. PCT/US20/48040 filed Aug. 26, 2020, which is related to and claims the benefit of U.S. Provisional Application 62/891,954, filed Aug. 26, 2019, and titled "Diagnosis of Tuberculosis and Other Diseases Using Exhaled Breath," and U.S. Provisional Application 63/069,120, filed Aug. 23, 2020, and titled "Diagnosis of Tuberculosis and Other Diseases Using Exhaled Breath," which are both hereby incorporated by reference in each of their entireties.

FEDERALLY SPONSORED RESEARCH AND DEVELOPMENT

None.

FIELD

This disclosure relates to methods and devices for analyzing exhaled breath aerosols and exhaled breath condensates using various diagnostic tools to enable rapid, low cost and autonomous point of care assays for several diseases including respiratory tract diseases. More particularly, but not by way of limitation, the present disclosure relates to methods and devices for analyzing exhaled breath aerosols and exhaled breath condensates for tuberculosis diagnosis using mass spectromtery, including MALDI-MS.

BACKGROUND

Tuberculosis (TB) has surpassed HIV/AIDS as a global killer with more than 4000 daily deaths. (Patterson, B., et al., 2018). The rate of decline in incidence remains inadequate at a reported 1.5% per annum and it is unlikely that treatment alone will significantly reduce the burden of disease. In communities with highly prevalent HIV, *Mycobacterium tuberculosis* (Mtb) genotyping studies have found that recent transmission, rather than reactivation, accounts for the majority (54%) of incident TB cases. The physical process of TB transmission remains poorly understood and the application of new technologies to elucidate key events in infectious aerosol production, release, and inhalation, has been slow. Empirical studies to characterize airborne infectious particles have been sparse. Two major difficulties plaguing investigation are the purportedly low concentrations of naturally produced Mtb particles, and the complication of environmental and patient derived bacterial and fungal contamination of airborne samples. There have nonetheless been a number of attempts at airborne detection. A 2004 proof of concept study and subsequent feasibility study in Uganda sampled cough-generated aerosols from pulmonary TB patients. Coughing directly into a sampling chamber equipped with two viable cascade impactors resulted in positive cultures from more than a quarter of participants despite their having received 1-6 days of chemotherapy. A follow-up work employing the same apparatus found that participants with higher aerosol bacillary loads could be linked to greater household transmission rates and development of disease findings which suggest that quantitative airborne sampling may serve as a clinically relevant measure of infectivity. Therefore, interruption of transmission would likely have a rapid, measurable impact on TB incidence.

The best method to control transmission of tuberculosis is to promptly identify and treat active TB cases. (Wood, R. C., et al., 2015). Diagnosis of pulmonary TB is usually done by microbiological, microscopic, or molecular analysis of patient sputum. The "gold standard" test for TB infection in most of the developing world is a smear culture based on a sputum sample. The sample is smeared onto a culture plate, a stain is added that is specific to Mtb, and the stained cells are counted using a microscope. If the concentration of cells in the smear is greater than a set threshold, then the sample is classified as positive. If the TB counts are below this threshold, it is classified as negative. Diagnosis may take several hours. The need for sputum as a diagnostic sample is a limiting factor due to the challenges of collecting it from patients and to its complex composition. The viscosity of the material restricts test sensitivity, increases sample-to-sample heterogeneity, and increases costs and labor associated with testing. Moreover, sputum production (which requires coughing) is an occupational hazard for healthcare workers. Sputum has several drawbacks as a sample medium. First, only about 50% of patients can provide a good sputum sample. For example, children under about age of eight often are not able to produce a sample upon request, usually because they have not developed an ability to "cough up" sputum from deep in their throat. The elderly and ill may not have the strength to cough up sputum. Others simply may not have sputum in their throat. Thus, a diagnostic method based on sputum analysis may not provide a diagnosis in as many as 50% of the patients who provide a sputum sample. Sputum is also not useful as a diagnostic sample if it is collected one to two days after a person has been treated with antibiotics because the sample is no longer representative of the disease state deep in the lungs, and within several days after treatment begins, the number of live Mtb in the sputum is significantly reduced. Urine and blood have been proposed as sample media for the diagnosis of TB infection. Blood is highly invasive and entails the higher cost of handling blood samples that are often HIV positive since, in some parts of the world, many TB patents also have HIV co-infections. Further, a patient with an active TB infection may not have many TB cells circulating in their blood. Urine-based diagnostics have also been proposed, but these tests look for biomarkers of the disease other than living TB bacilli, and none not been validated for widespread clinical use.

A sample that is easier, safer, and more uniform to collect and handle would simplify TB diagnosis. Exhaled breath contains aerosols ("EBA") and vapors that can be collected noninvasively and analyzed for characteristics to elucidate physiologic and pathologic processes in the lung. (Hunt, 2002). To capture the breath for assay, exhaled air is passed through a condensing apparatus to produce an accumulation of fluid that is referred to as exhaled breath condensate ("EBC"). Although predominantly derived from water vapor, EBC has dissolved within its nonvolatile compounds, including cytokines, lipids, surfactant, ions, oxidation products, and adenosine, histamine, acetylcholine, and serotonin. In addition, EBC traps potentially volatile water-soluble compounds, including ammonia, hydrogen peroxide, and ethanol, and other volatile organic compounds. EBC has readily measurable pH. EBC contains aerosolized airway lining fluid and volatile compounds that provide noninvasive indications of ongoing biochemical and inflammatory activities in the lung. Rapid increase in interest in EBC has resulted from the recognition that in lung disease, EBC has measurable characteristics that can be used to differentiate between infected and healthy individuals. These assays have provided evidence of airway and lung redox deviation, acid-base status, and degree and type of inflammation in acute and chronic asthma, chronic obstructive pulmonary disease, adult respiratory distress syndrome, occupational diseases, and cystic fibrosis. Characterized by uncertain and variable degrees of dilution, EBC may not provide precise assessment of individual solute concentrations within native airway lining fluid. However, it can provide useful information when concentrations differ substantially between health and disease or are based on ratios of solutes found in the sample.

Patterson et al. (2018) used a custom-built respiratory aerosol sampling chamber (RASC), a novel apparatus designed to optimize patient-derived exhaled breath aerosol sampling, and to isolate and accumulate respirable aerosol from a single patient. Environmental sampling detects the Mtb present after a period of ageing in the chamber air. 35 newly diagnosed, GeneXpert (Cepheid, Inc., Sunnyvale, CA) sputum-positive, TB patients were monitored during one-hour confinement in the RASC chamber which has a volume of about 1.4 $m^3$. The GeneXpert genetic assay is based on polymerase chain reaction (PCR) and may be used to analyze a sample for TB diagnosis and to indicate whether or not there are drug resistance genes in the TB sample. The GeneXpert PCR assay for TB can accept a sputum sample and provide a positive or negative result in about one hour. The chamber incorporated aerodynamic particle size detection, viable and non-viable sampling devices, real-time $CO_2$ monitoring, and cough sound-recording. Microbiological culture and droplet digital polymerase chain reaction (ddPCR) were used to detect Mtb in each of the bio-aerosol collection devices. Mtb was detected in 77% of aerosol samples and 42% of samples were positive by mycobacterial culture and 92% were positive by ddPCR. A correlation was found between cough rate and culturable bioaerosol. Mtb was detected on all viable cascade impactor stages with a peak at aerosol sizes 2.0-3.5 μm. This suggests a median of 0.09 CFU/litre of exhaled air for the aerosol culture positives and an estimated median concentration of $4.5\times10^7$ CFU/ml of exhaled particulate bio-aerosol. Mtb was detected in bioaerosols exhaled by a majority of the untreated TB-patients using the RASC chamber. Molecular detection was found to be more sensitive that Mtb culture on solid media.

Mtb can be identified in EBA by culture, ddPCR, electron microscopy, immunoassay, and cell staining (e.g., oramine and dmnTre). Of these, PCR and immunoassays have the potential to be rapid and specific to the species level. PCR and other genomics-based techniques can be specific to the strain level. Mass spectrometry has also been shown to be specific to the strain level for cultures obtained from bacterial infections. For example, the Biotyper from Bruker Daltonics (Germany), has been shown to be able to identify up to 15,000 strains of bacteria that cause infections in humans. These techniques have been shown to be capable of identifying TB infection from EBA. Immunoassays for Mtb detection, such as the one based on lipoarabinomannan, are also well known.

In the case of TB, people infected with TB are often diagnosed through passive case finding when individuals present themselves to clinics. Active case finding ("ACF") is generally considered to include other methods of reaching people suspected of TB infection outside of the primary health care system. According to WHO, ACF is "systematic identification of people with suspected active TB, using tests, examinations, or other procedures that can applied rapidly." The goal of ACF is to get those infected to treatment earlier, reducing the average period of infection, and thereby reducing the spread of the disease. In the case of TB, by the time an individual goes to a clinic for help, that person may have transmitted the TB infection to between about 10 other people and about 115 other people. ACF can help to reduce or prevent significant TB transmission. The diagnostic systems and methods such as sputum analysis and blood analysis are either not automated and autonomously operated, or not rapid. Many have expensive assays that are consumed for each analysis, and thus, do not have general utility for active case finding, particularly in developing and under-developed countries. As previously described, EBA analysis appears to be a compelling diagnostic tool for TB detection that provides for rapid analysis, portability, and low cost because the need for expensive assays and consumables are eliminated. McDevitt et al. (2013) have report EBA analytical devices and methods for influenza diagnosis. An impactor is used to remove large particles (>4 μm) from exhaled breath, followed by a wetted-film collector for the smaller particles (<4 μm). The two size bins of collected particles were analyzed for influenza virus using a genomics-based method, reverse transcriptase polymerase chain reaction (rt-PCR). PCR technology uses biomolecular probes, combined with other biomolecules including enzymes, to amplify a specific sequence of DNA if that particular sequence is present in the sample. The targeted sequences are believed to be specific to the disease being identified. McDevitt et al. showed that EBA samples can be used to diagnose influenza. The disclosed devices and methods have several shortcomings from a practical standpoint. First, the breath aerosol sample is collected into discrete samples that are several milliliters in volume, and thus, considerable effort is needed to concentrate the sample. Further, the diagnostic device is not coupled to or integrated with the sample collector and is not amenable for use as an ACF tool. The ability to automate the RNA assays to create an autonomous diagnostic tool for TB analysis is not clear. A method to determine whether sufficient volume of cough or breath aerosol was generated by a particular patient is not described. As a result, if a sample is found to be negative for influenza it may be due to a false negative resulting from inadequate sample collection. It is well known that there are large variabilities among humans with respect to the volume of aerosolized lung fluid produced during various breathing maneuvers.

The GeneXpert Ultra is a state-of-the-art genomics-based point of care diagnostic device which uses PCR technology. It may be integrated with an EBA sample collection method to perform ACF of TB and other respiratory diseases, but the sample collection times would be too long to be practical. Patterson et al. have shown that between 20 and 200 TB bacilli are typically produced in EBA and can be collected over a one-hour sampling period. A minimum of one hour of sampling would be required to use the GeneXpert Ultra as a diagnostic assay. The GeneXpert may be integrated with a system that samples air to analyze air samples for airborne pathogens. The BDS system (Northup Grumman, Edgewood, MD), is being used for screening US Postal Service mail for bacterial spores that cause anthrax as the mail passes through distribution centers. It combines a wetted-wall cyclone with a GeneXpert PCR system to autonomously sample air and report if pathogens are present. However, the GeneXpert Ultra assay has a relatively high cost per test and takes approximately an hour to complete the assay and provide a result. In general, PCR-based diagnostics are unsuitable for TB screening for ACF applications due to both the extended time needed for sampling and analysis, and the relatively high cost per test.

The time associated with a diagnostic assay is a critical parameter for a fielded, or "point of care" test. ACF is an example of a fielded diagnostic assay because, by definition, ACF takes place outside the healthcare system. In the U.S., a point-of-care test needs to provide an answer in 20 minutes or less. If not, the test is considered to be too slow and not acceptable for achieving short patient wait-times. In the developing world, and especially in countries with a history of TB prevalence, the GeneXpert may be used to provide diagnosis in about one hour. As previously described, this assay is expensive to implement on a "cost per test" basis, and therefore it is not yet widely deployed. Because of high cost, it is not used to screen patients who appear healthy (non-symptomatic) but might have TB infection, but rather, is used to confirm a diagnosis that is strongly suspected based on other tests or factors.

Fennelly et al. (2004) described TB analysis using cough aerosol and a collection chamber that contains two Anderson cascade impactors using individuals who were known to have active patients. Individuals were asked to provide two discrete five-minute bursts of intense coughing. Culturing of impacted samples took 30-60 days, and therefore this approach is not amenable to automation. A challenging aspect of EBA as a clinical sample is the relatively small sample of volume of exhaled particulates that can be collected from breath. Further, a significant fraction of the mass collected is water. The molecules that contain diagnostic information ("biomarkers") are present in nanoliter or picogram quantities. Subsequently, the aerosol collection method must be effective in capturing a large fraction of the biomass in the exhaled breath. Exhaled breath includes air that is exhaled from the lungs through any number of maneuvers, including tidal breathing, deep breathing, coughing, and sneezing. Particular types of deep breathing maneuvers such as forced vital capacity (FVC), may be used to measure the maximum volume of lung capacity by breathing in as much as possible, and exhaling as far (or as deep) as possible to maximize the volume of exhaled breath. Forced expiratory volume (FEV) measures how much air a person can exhale during a forced breath. The amount of air exhaled may be measured during the first (FEV1), second (FEV2), and/or third seconds (FEV3) of the forced breath. Forced vital capacity (FVC) is the total amount of air exhaled during an FEV test. Forced expiratory volume and forced vital capacity are lung function tests that are measured during spirometry. Forced expiratory volume is an important measurement of lung function.

Although research has shown that respiratory diseases can be detected from breath aerosol and breath condensate, modern clinical tests for infections or diseases such as tuberculosis, influenza, pneumonia continue to utilize sputum, blood, or nasal swabs. Exhaled breath analytical tools have not been commercialized because methods and devices to efficiently collect and concentrate the trace amounts of analyte present in exhaled breath are lacking. Furthermore, there is no standard or methodology to assess how much exhaled breath is sufficient for a particular diagnosis. The disclosed exemplary devices and methods overcome these limitations by collecting exhaled breath aerosol and breath condensate at high flow rate, high efficiency, and into relatively concentrated samples. Further, size sorting of aerosol can be incorporated to increase the signal to noise ratio for specific analytes prior to collection of the analytes. The concentrated samples may then be analyzed by several methods, but preferably, using methods that are sensitive, rapid, and highly specific to the analytes of interest. More preferably, the analysis will be rapid, and near real-time. Mass spectrometry, real-time PCR, and immunoassays have the highest potential to be sensitive, specific and nearly real-time.

A need exists for sample collection methods that can be coupled with fast diagnostic tools such as mass spectrometry ("MS") that is more rapid and reliable than sputum analysis and less invasive than blood analysis to provide a diagnostic assay that is fast, sensitive, specific and preferably, characterized by low cost per test. Such a system could be used for active case finding (ACF) of TB and other lung or respiratory tract diseases. To be effective, a system for ACF must be rapid and inexpensive on a "per diagnosis" basis. Low cost-per-test is a requirement for screening a large number of individuals to proactively prevent TB transmission to search for the few that are indeed infected TB. Low cost devices and methods would also be required for point-of-care diagnosis of influenza and other pathogenic viruses because patients probably infected with a "common cold" may be infected with rhinovirus. In some cases, the respiratory infection will be driven by a bacterial or fungal microbe and may be treatable with antibiotics. In other cases, the microbe may be resistant to antibiotics, and a diagnostic method that can identify microbial resistance to antibiotics is preferable. Rapid EBA methods for distinguishing between viral and bacterial infections in the respiratory tract are desired while minimizing the occurrence of false negatives due to an insufficient sample volume. Mass spectrometry, genomics methods including PCR, and immunoassays have the highest potential to be sensitive and specific. Mass spectrometry, and in particular, MALDI time-of-flight mass spectrometry (MALDI-TOFMS), is a preferred diagnostic tool for analysis EBA and EBC samples because it has been demonstrated to be sensitive, specific and near real-time.

BRIEF DISCLOSURE

Disclosed in an exemplary system for diagnosing respiratory diseases in an individual using exhaled breath comprising a sample extraction component configured to receive an individual's face for extracting breath aerosol (EBA) particles expelled from the individual during a predetermined number of breath maneuvers into a flow of air fed into the extraction component, a sample capture component comprising, means to collect the EBA particles into a collected liquid sample, and, a packed bed column to selectively capture the EBA particles from the collected liquid sample onto the packed bed, means to elute the collected EBA particles from the packed bed using one or more solvents, and, a diagnostic device for analyzing the EBA particles comprised in the one or more solvents. The EBA particles may comprise at least one of microbes, virus, metabolite biomarkers, lipid biomarkers, and proteomic biomarkers characteristic of the respiratory disease. The flow rate of air entering the sample capture component may be between about 50 L/min and about 500 L/min. The volume of the collected sample may be between about 100 microliter and about 10 ml. The means to collect the EBA particles may comprise an air pump and an impactor wherein the air pump provides the flow of air to carry the exhaled breath from the extraction component into the impactor and wherein the impactor separates the EBA particles from exhaled breath to produce the collected sample. The impactor may comprise at least one of a cyclone, a wetted wall cyclone, one or more wetted film impactors, a virtual impactor, and an impinger. The sample extraction component may comprise at least one of a cone shaped device, a shroud, CPR rescue mask, a CPAP mask, a ventilator mask, and a medical universal mouthpiece. The diagnostic device may comprise at least one of PCR, rt-PCR, immuno-based assay, mass spectrometer (MS), MALDI-MS, ESI-MS, GC-MS, GC-IMS and MALDI-TOFMS. The exemplary system may further comprise one or more chilling devices configured to be in thermal communication with the means to collect the EBA particles. The means to collect the EBA particles may be chilled to a temperature greater than about 0° C. and less than about 10° C. using the one or more chilling devices. The means to collect the EBA particles may be chilled to a temperature greater than about 0° C. and less than about 4° C. using the one or more chilling devices. The system may further comprise one or more sensors configured be in fluid communication with the sample extraction component wherein the output of the one or more sensors is used to calculate the total cumulative volume of exhaled breath aerosol particles entering the sample capture component. The one or more sensors may comprise at least one of a $CO_2$ sensor, an oxygen sensor, a humidity sensor, an optical particle size counter, an aerodynamic particle sizer, and a nephelometer. The collected sample may be transferred to the packed bed column using at least one of a dispensing pump and a robotic sample transfer system. The lipid biomarkers may comprise biomarkers characteristic of Mtb. The packed bed column may comprise solid particles comprising at least one of resins, cellulose, silica, agarose, and hydrated $Fe_3O_4$ nanoparticles. The packed bed column may comprise resin beads having C18 functional groups on the surface. The resin beads may have a nominal diameter of between about 12 μm and about 20 μm. The weight of the packed bed may be about 25 mg. The means to elute the collected EBA particles from the packed bed may comprise at least one of one or more syringes, and one or more pumps. The solvent may comprise at least one of acetonitrile, methanol, acid, isopropanol, the remaining being water.

Disclosed is an exemplary method for diagnosing respiratory diseases in an individual using exhaled breath comprising extracting EBA particles expelled into a flow of air fed into a sample extraction component configured to receive an individual's face, collecting the EBA particles from exhaled breath and air as a collected liquid sample, capturing the EBA particles in the collected liquid sample using a packed bed column to selectively capture the EBA particles from the collected liquid sample onto the packed bed, and, eluting the collected EBA particles from the packed bed using one or more solvents, and, analyzing the EBA particles comprised in the one or more solvents. The one or more solvents may comprise at least one of acetonitrile, methanol, acid, isopropanol, the remaining being water. The one or more solvents may comprise between about 50 vol.-% and about 70 vol.-% acetonitrile in water. The one or more solvents may comprise between about 50 vol.-% and about 70 vol.-% isopropanol in water. The eluting step may comprise washing the packed bed column with about 50 vol.-% ACN in a first step and with about 70 vol.-% IPA in a second step. The analysis step may further comprise detecting at least one of lipid biomarkers PS 24:4, PI 18:4, Cer 8:0, DG O-8:0, and PI 20:4 to determine the presence of absence of tuberculosis.

Other features and advantages of the present disclosure will be set forth, in part, in the descriptions which follow and the accompanying drawings, wherein the preferred aspects of the present disclosure are described and shown, and in part, will become apparent to those skilled in the art upon examination of the following detailed description taken in conjunction with the accompanying drawings or may be learned by practice of the present disclosure. The advantages of the present disclosure may be realized and attained by means of the instrumentalities and combinations particularly pointed out in the appendant claims.

DRAWINGS

The foregoing aspects and many of the attendant advantages of this disclosure will become more readily appreciated as the same becomes better understood by reference to the following detailed description, when taken in conjunction with the accompanying drawings, wherein:

FIG. 1. Schematic diagram of an exemplary EBA based diagnosis system.

Figure 2:
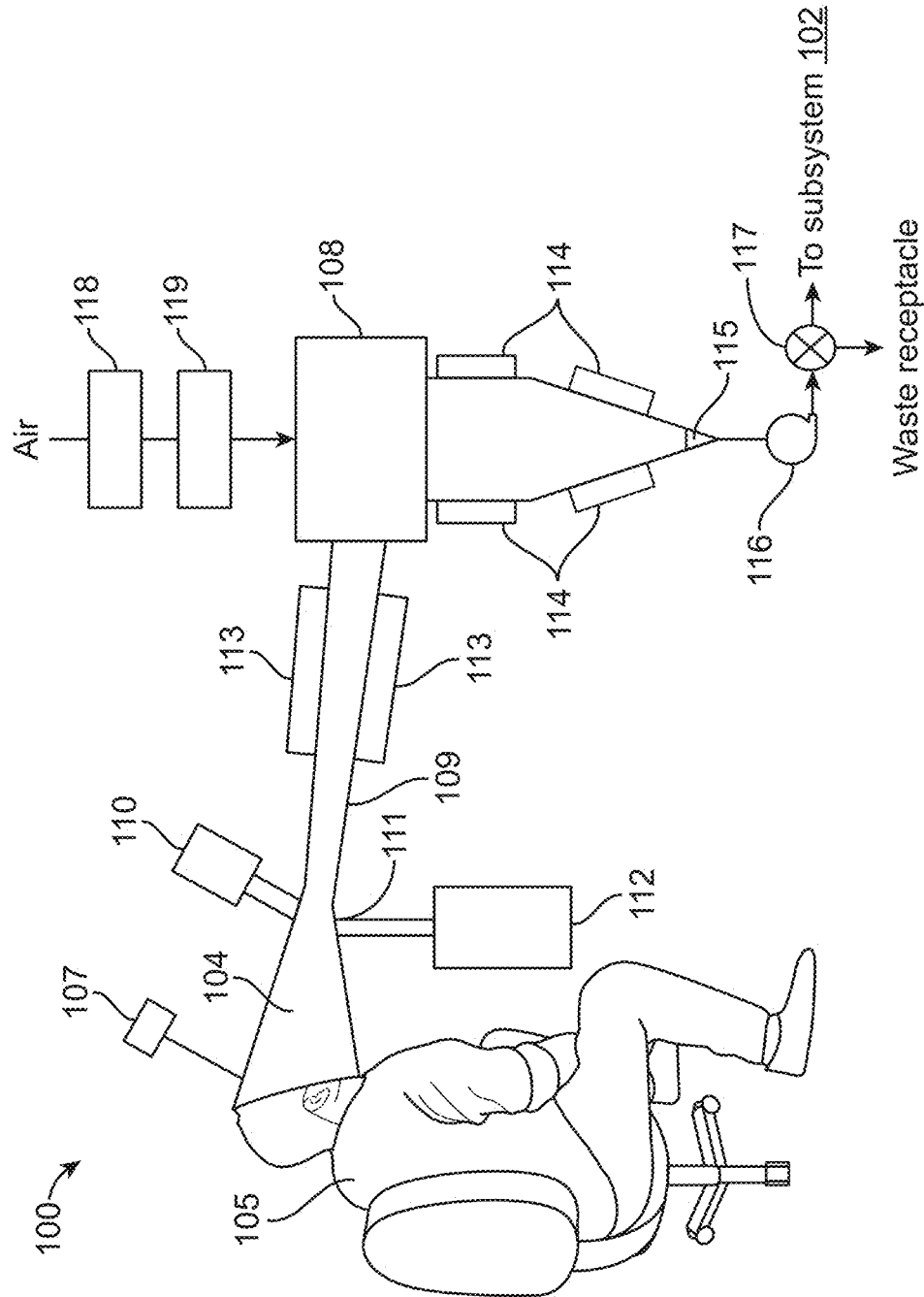

FIG. 2. Schematic diagram of an exemplary EBA sample collection subsystem.

Figure 3:
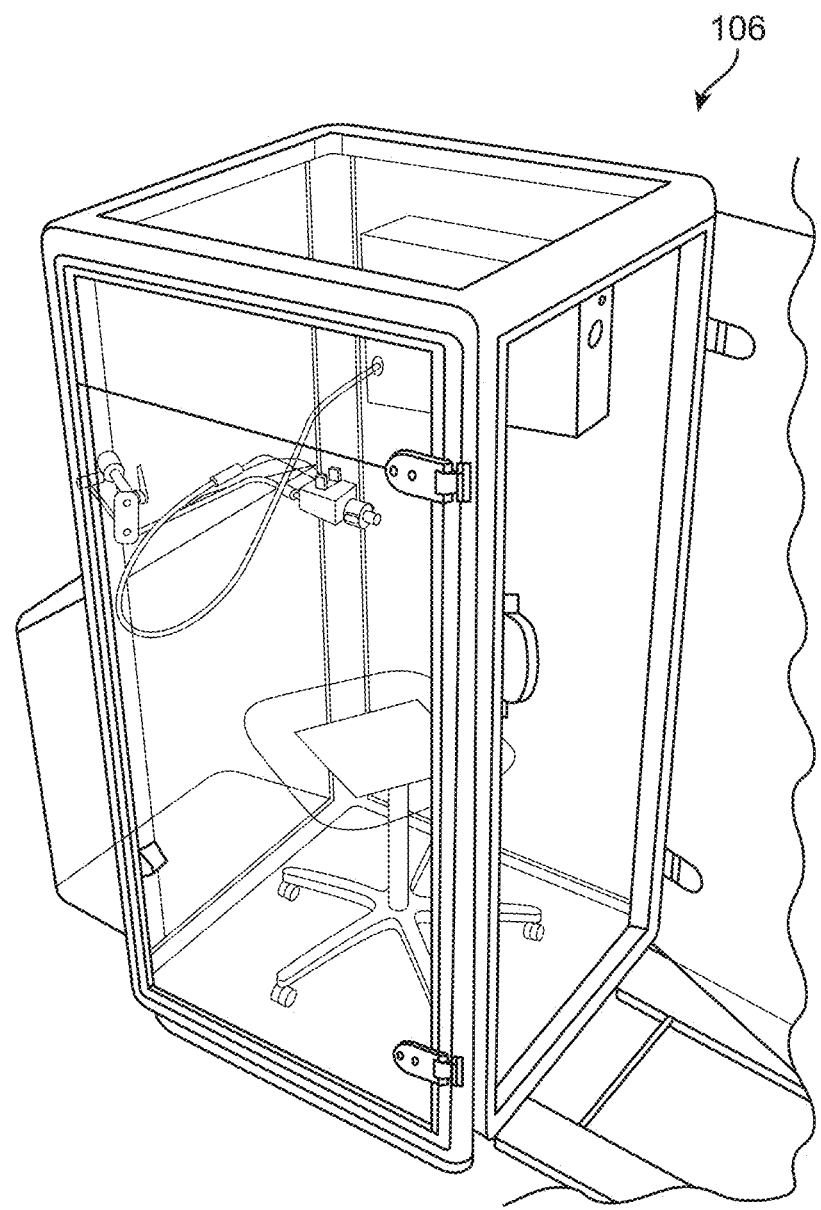

FIG. 3. Perspective view of a containment booth that may be optionally used in the EBA sample collection subsystem.

Figure 4A:
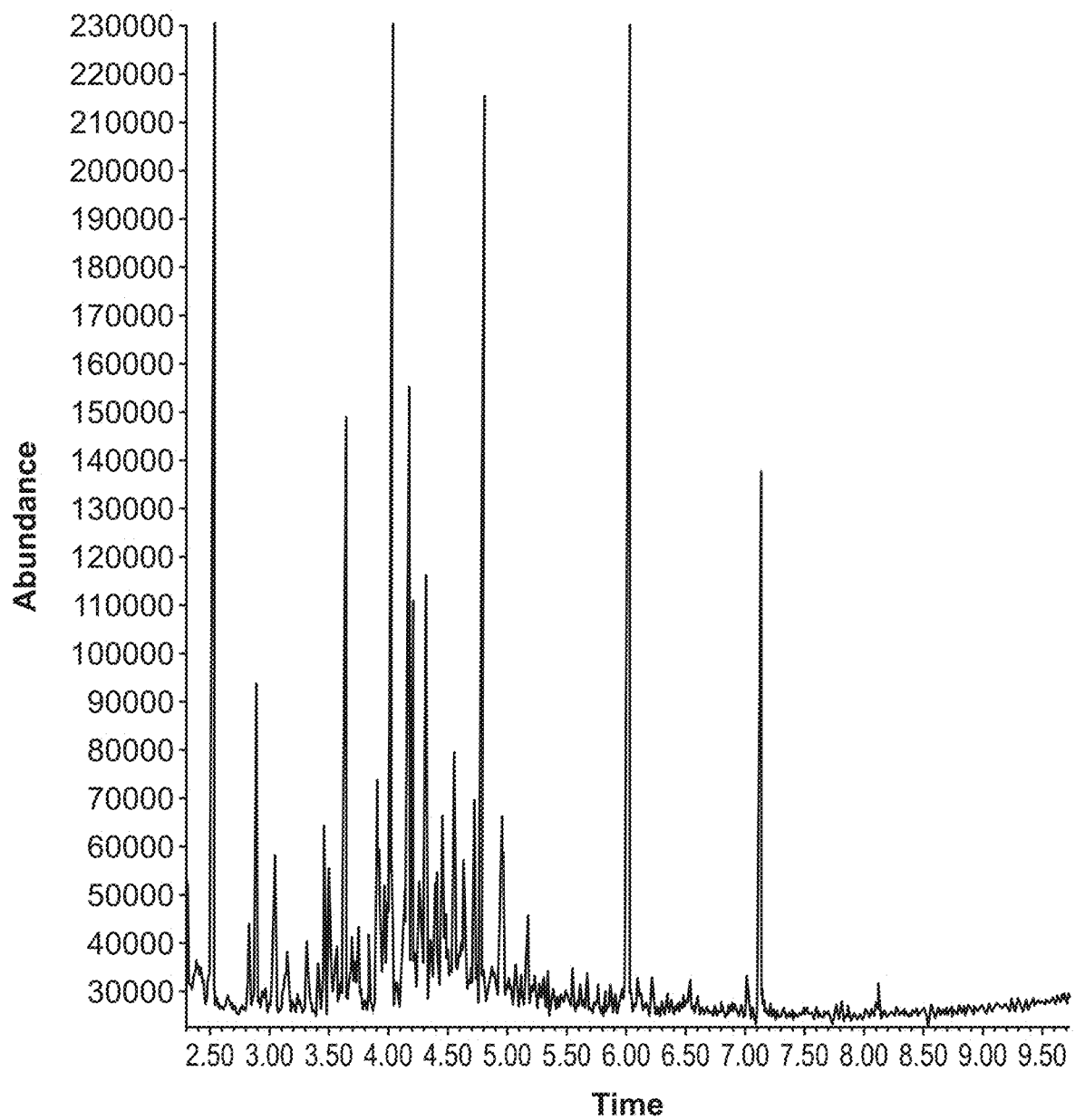
Figure 4B:
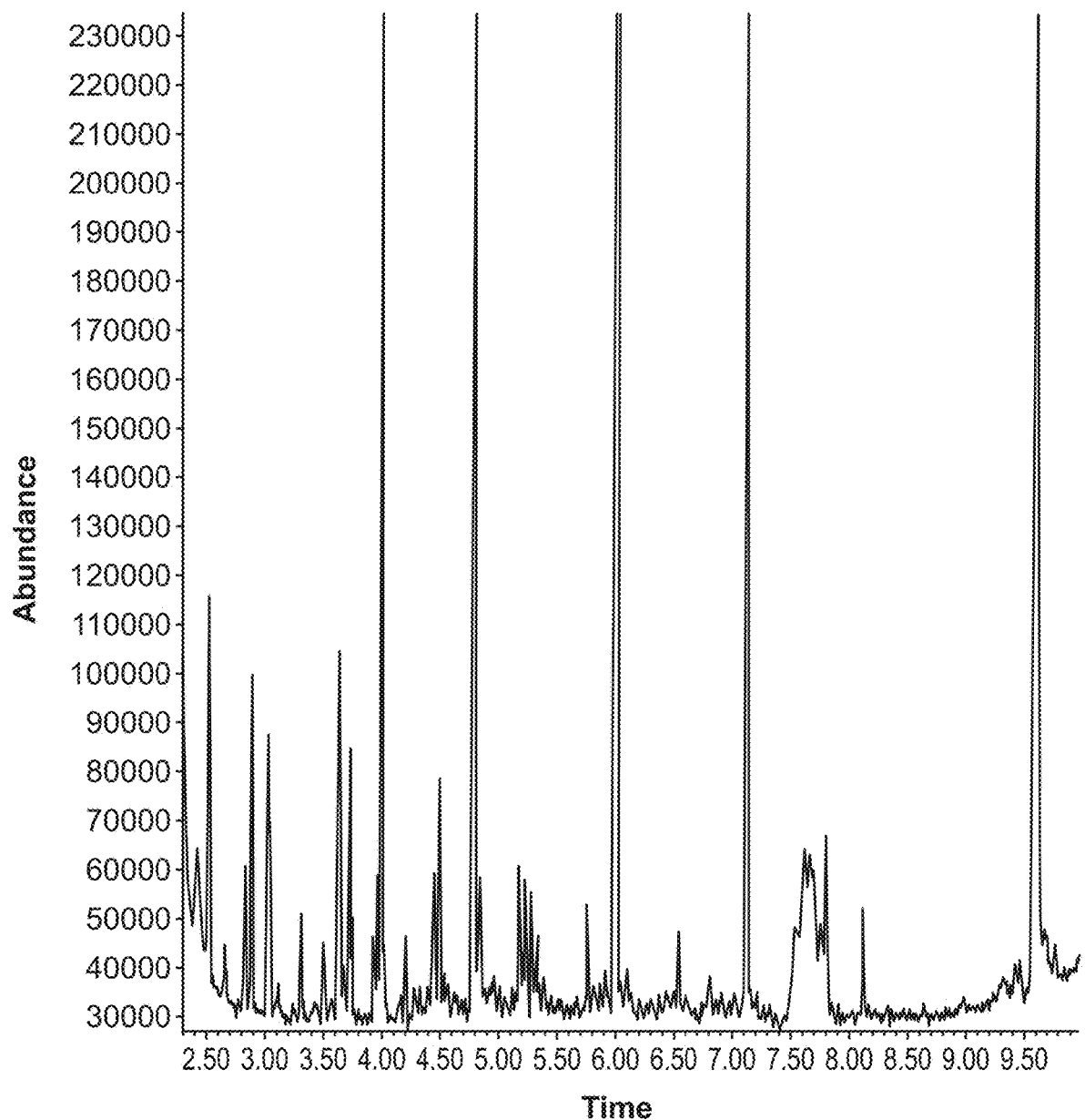

FIGS. 4A-B. Volatile organic compound in exhaled breath analysis—ion chromatograms showing differences in spectral signatures between TB (FIG. 4A) and non-TB patients (FIG. 4B)

Figure 5:
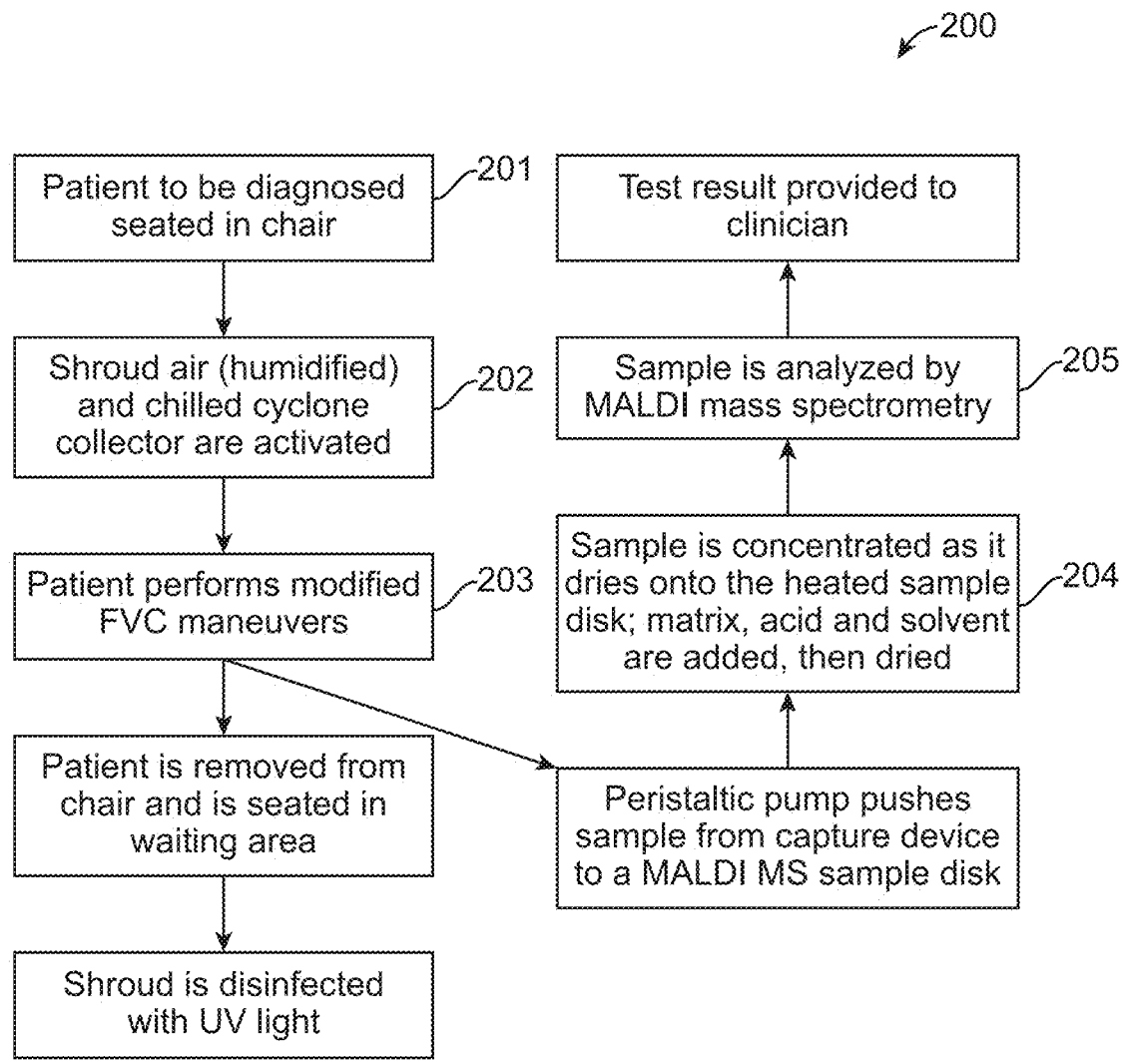

FIG. 5 is a schematic diagram of an exemplary diagnostic method using exhaled breath aerosol (EBA) and exhaled breath condensate (EBC) analysis.

Figure 6A:
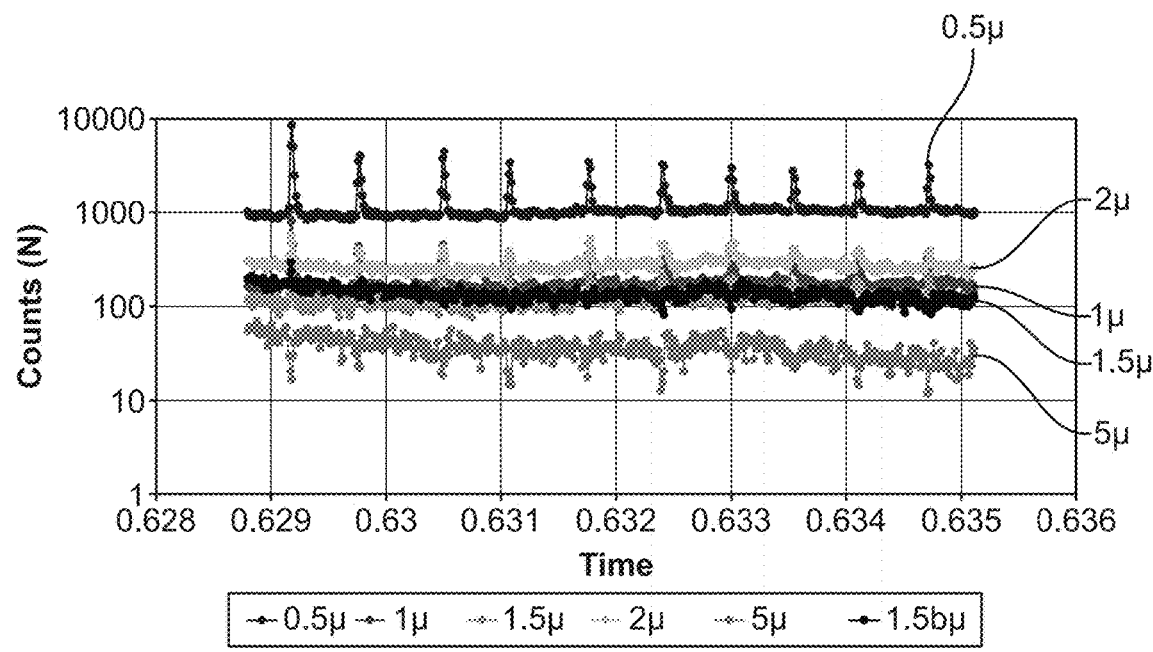
Figure 6B:
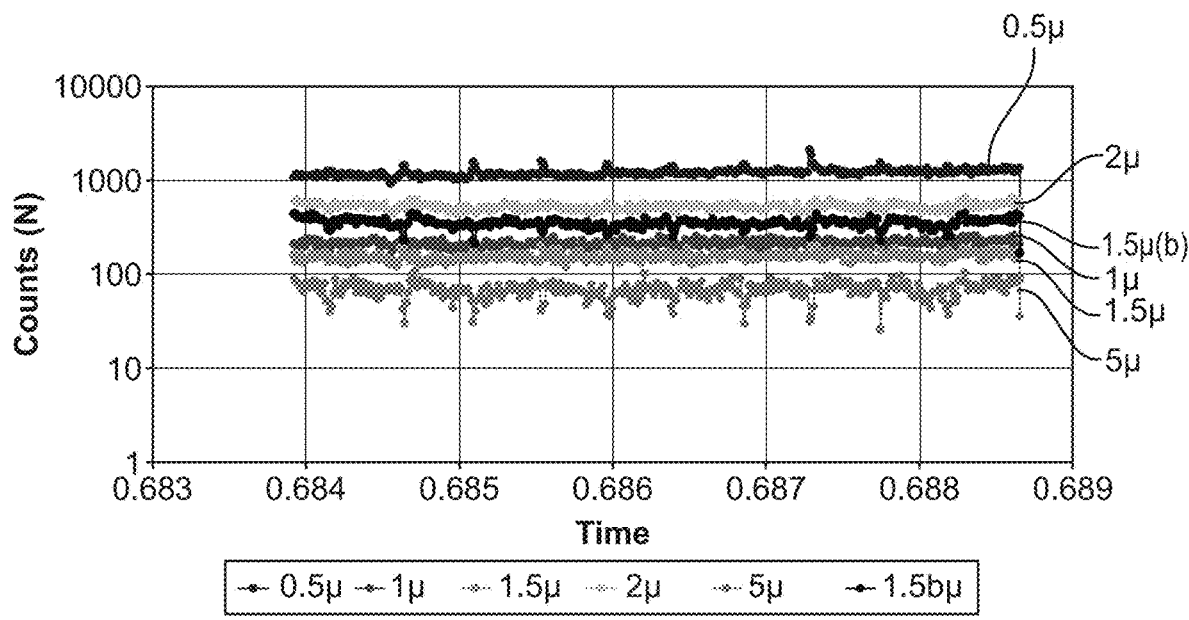
Figure 6C:
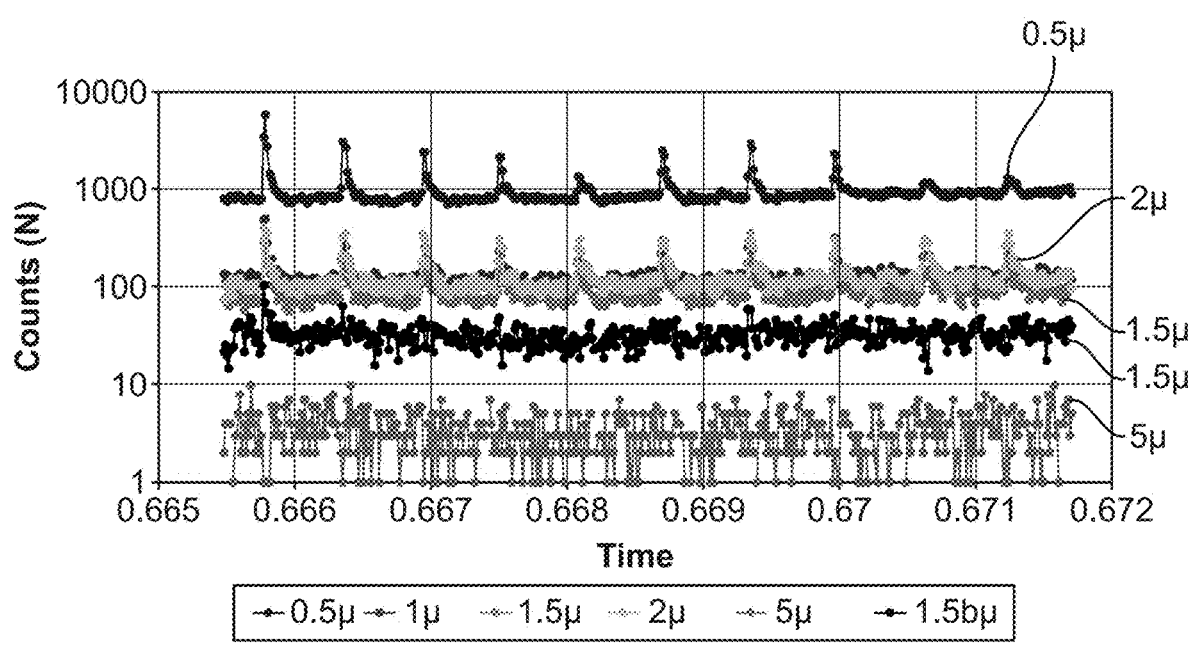

FIGS. 6A-C. Particle size distribution variability in exhaled breath from three healthy individuals using the modified FVC breathing maneuvers.

Figure 7:
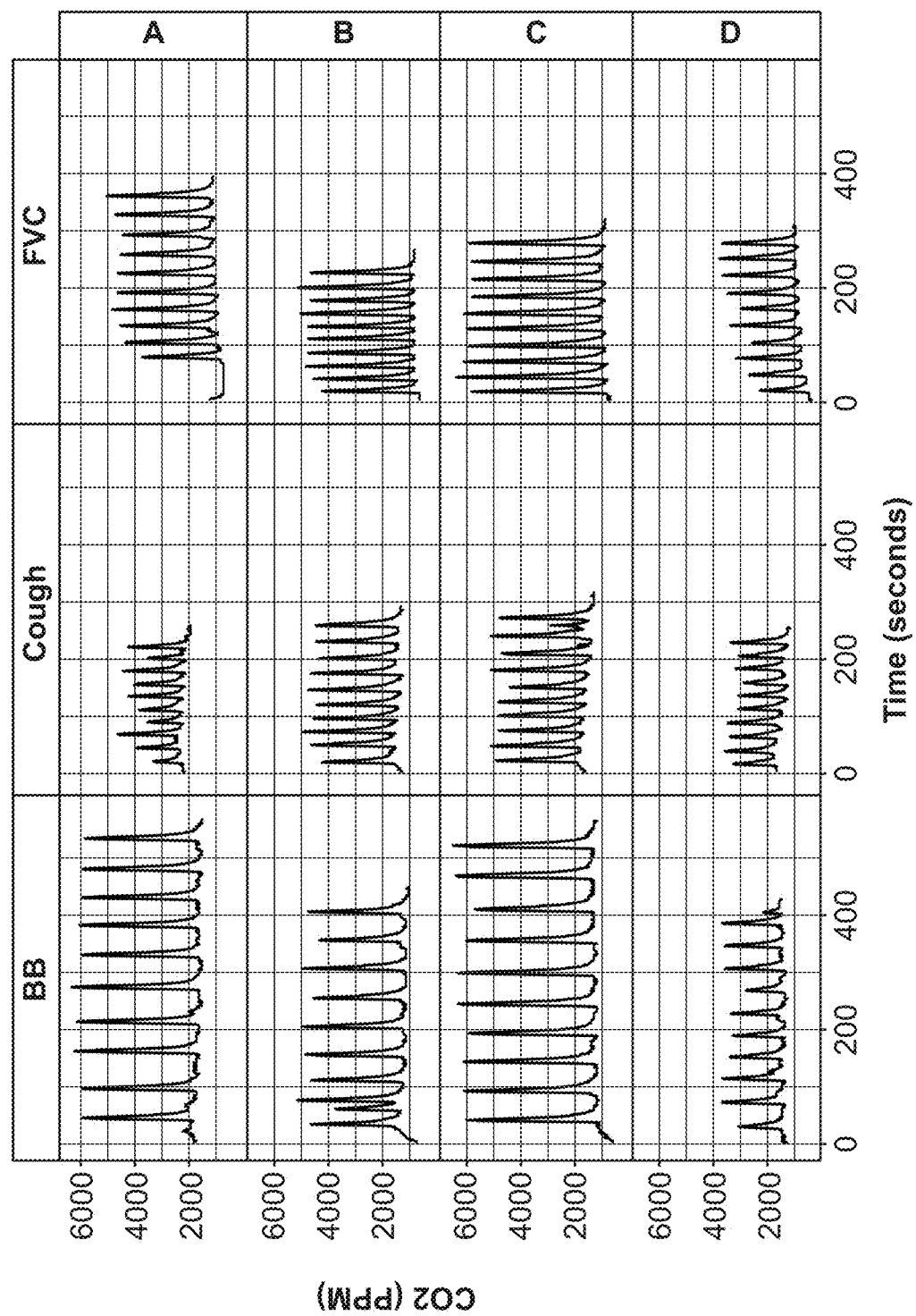

FIG. 7. Carbon dioxide measurements in exhaled breath during various breathing maneuvers.

Figure 8:
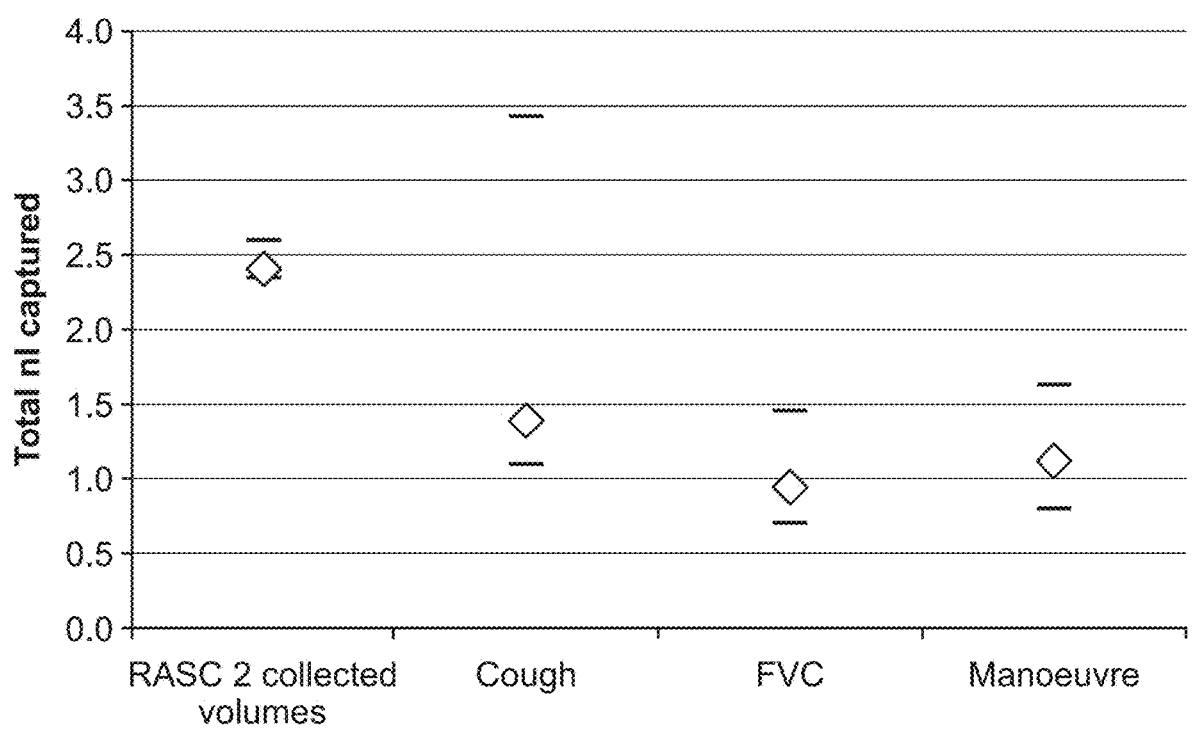

FIG. 8. Volume of lung fluid collected from exhaled breath during different breathing maneuvers.

Figure 9:
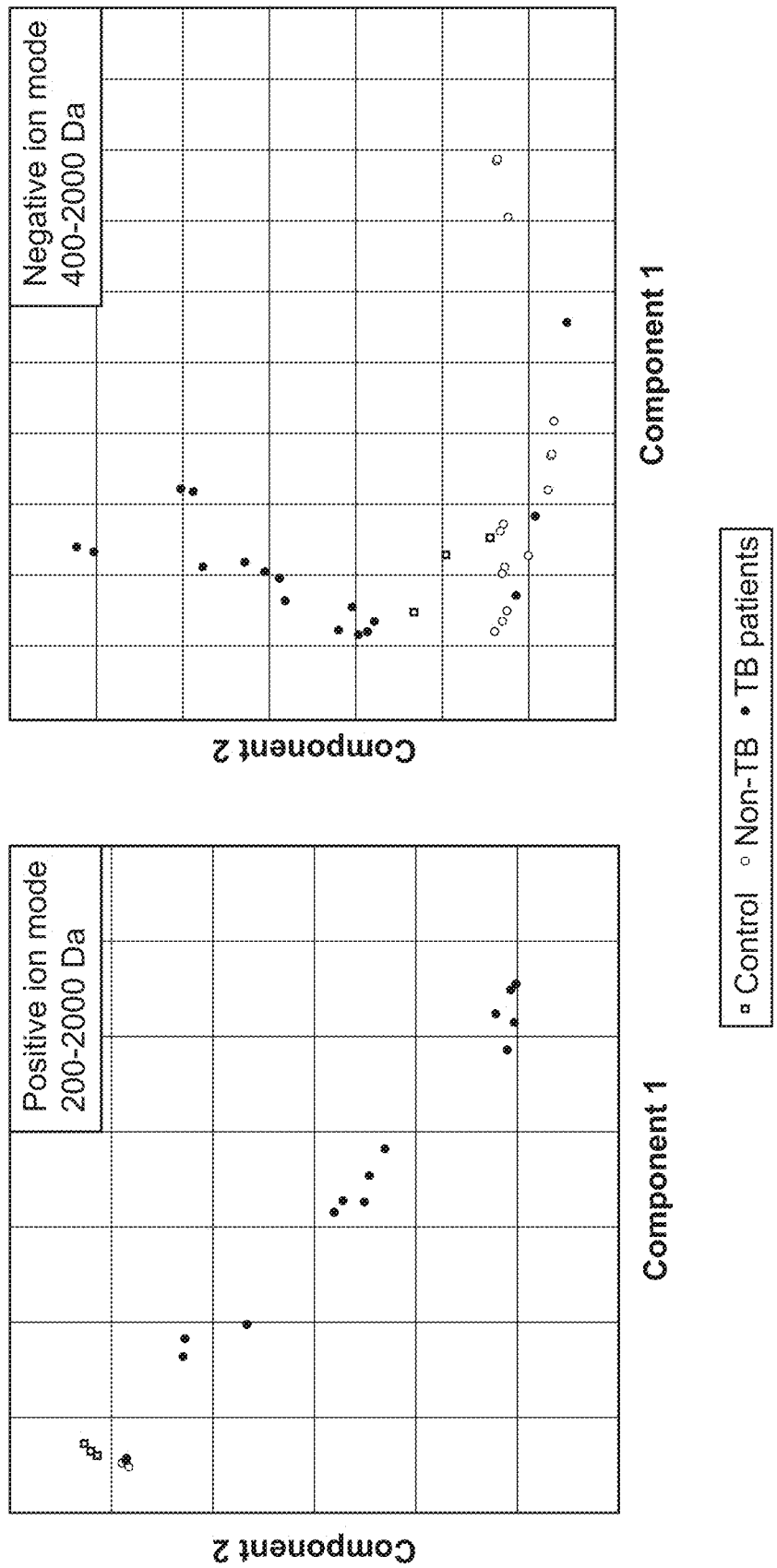

FIG. 9. Weighted principal component analysis (PCA) of MS signals acquired from positive and negative ion modes of TB and non-TB samples.

Figure 10:
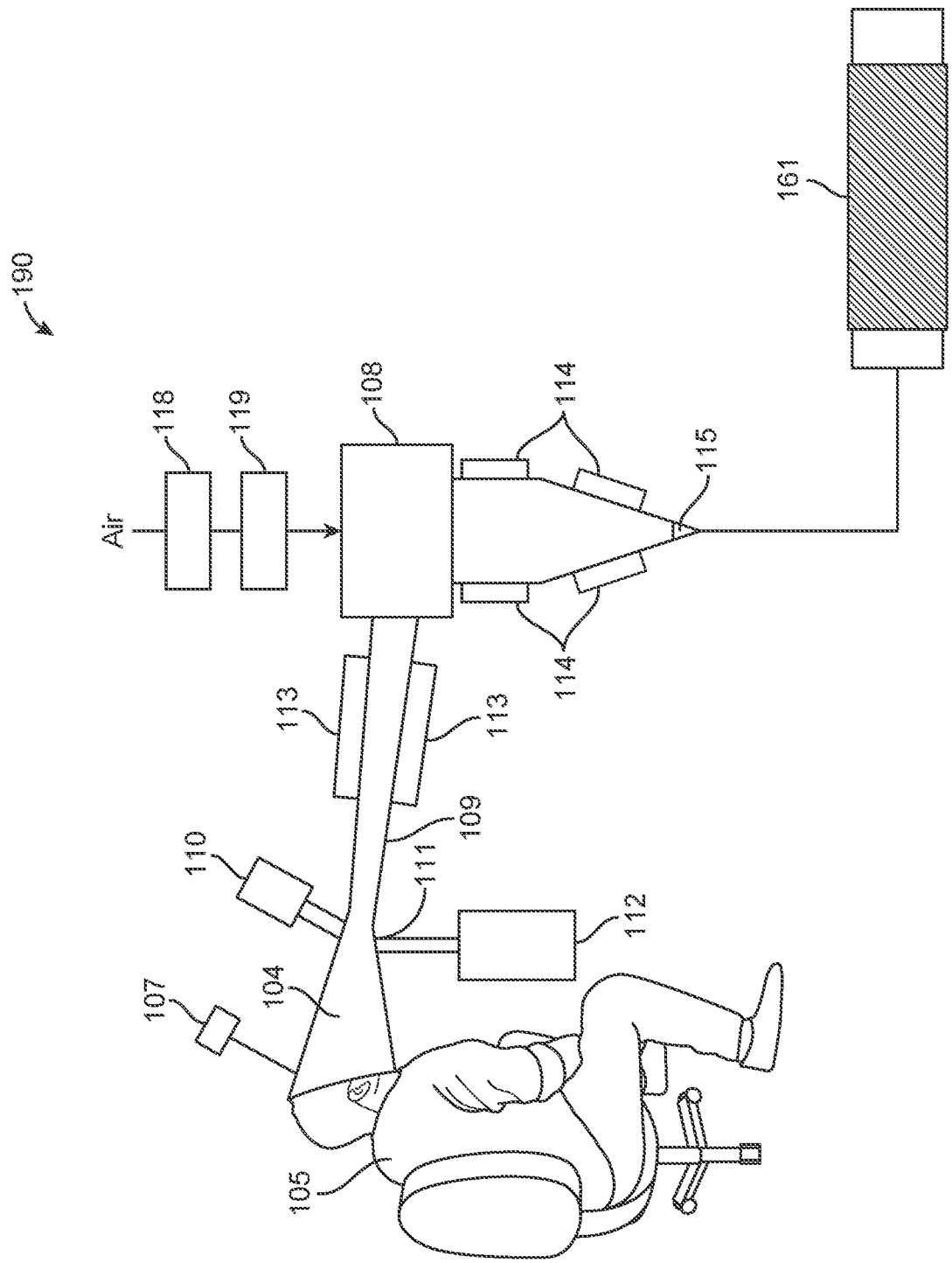

FIG. 10. Schematic diagram of an exemplary EBA sample collection subsystem.

FIGS. 11A-F. Total ion chromatogram of EBA and blank samples (A), representative total ion chromatogram of small metabolites in GXP positive and negative subjects (B), feature distribution of small metabolites in samples from GXP positive and GXP negative subjects (C), feature distribution of lipids in samples from GXP positive and negative subjects (D), dynamic range of small metabolites in EBA samples from all subjects (E), and dynamic range of lipids in EBA samples from all subjects (F).

Figure 12A:
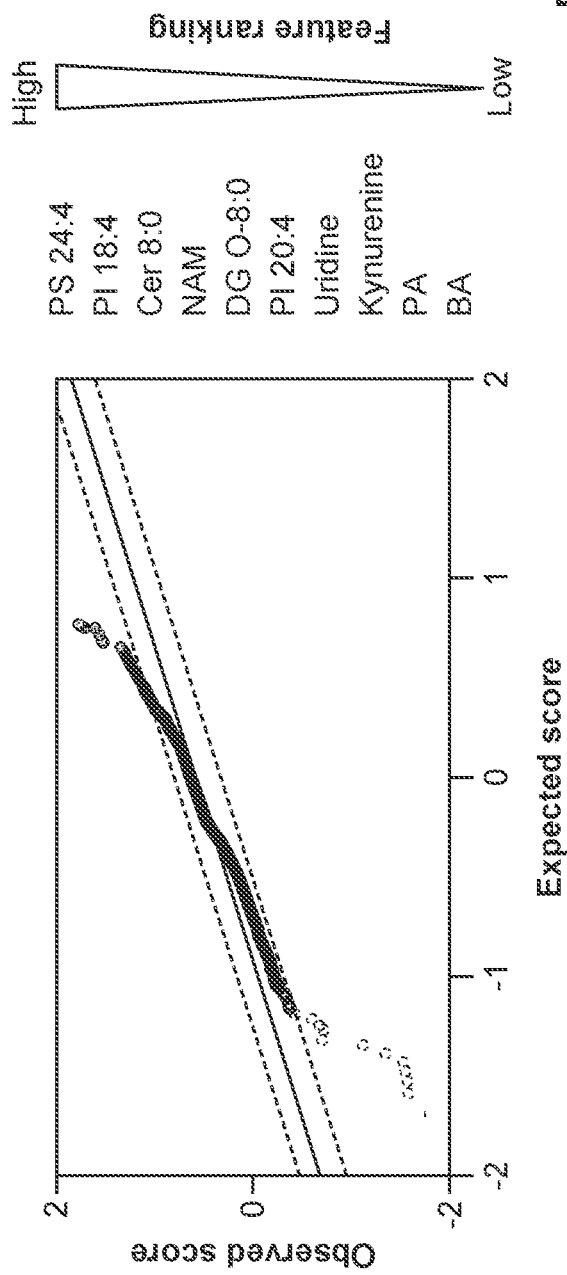
Figure 12B:
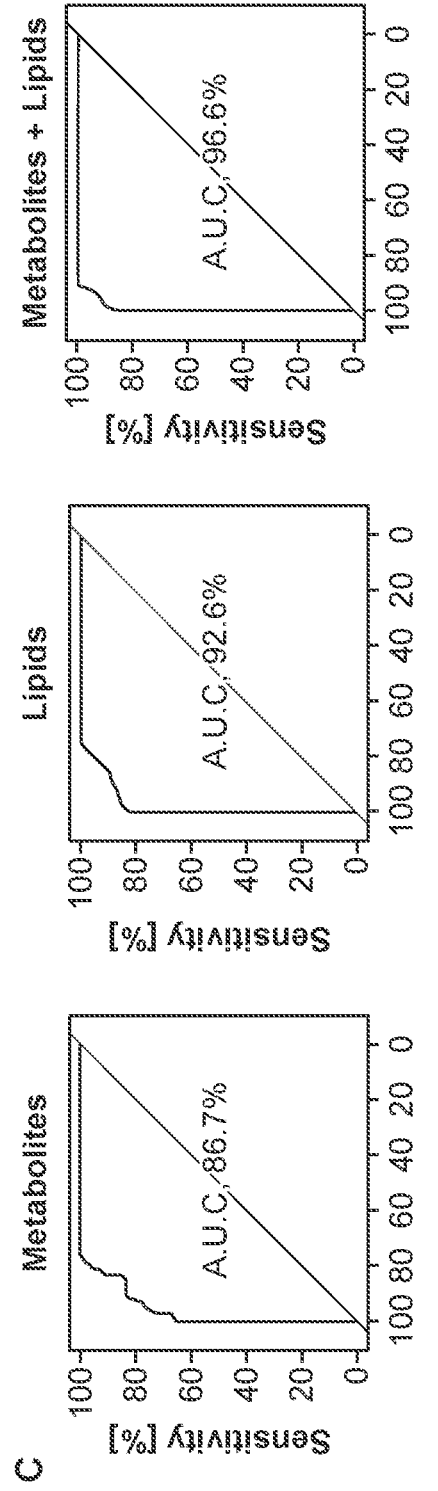

FIGS. 12A-B. (A) Feature ranking analysis of metabolites and lipids of statistical significance between GXP negative and positive groups based on significance analysis of microarrays (SAM), and (B) A.U.C. values calculated using regression models for the identified metabolites and lipid molecules.

Figure 13:
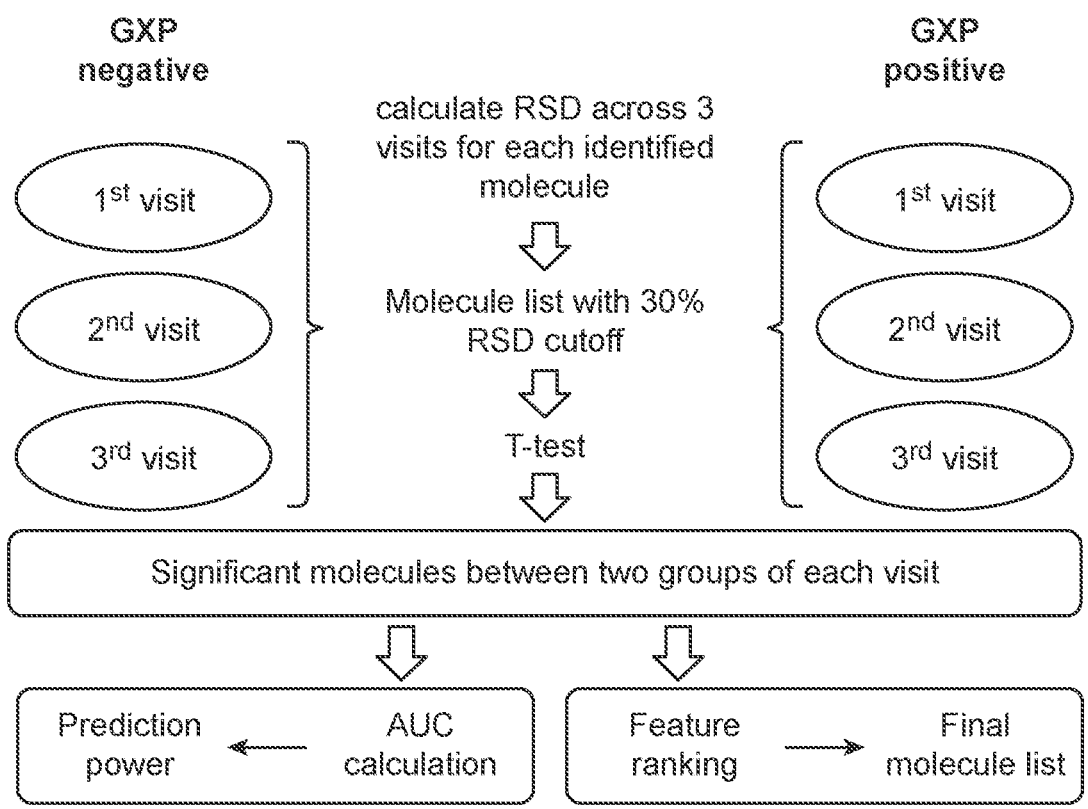

FIG. 13. Exemplary workflow for data analysis for analyzing EBA data related to metabolite and lipid biomarkers in EBA collected from TB subjects and healthy subjects.

All reference numerals, designators and callouts in the figures are hereby incorporated by this reference as if fully set forth herein. The failure to number an element in a figure is not intended to waive any rights. Unnumbered references may also be identified by alpha characters in the figures and appendices.

The following detailed description includes references to the accompanying drawings, which form a part of the detailed description. The drawings show, by way of illustration, specific embodiments in which the disclosed systems and methods may be practiced. These embodiments, which are to be understood as "examples" or "options," are described in enough detail to enable those skilled in the art to practice the present invention. The embodiments may be combined, other embodiments may be utilized, or structural or logical changes may be made, without departing from the scope of the invention. The following detailed description is, therefore, not to be taken in a limiting sense and the scope of the invention is defined by the appended claims and their legal equivalents.

In this disclosure, aerosol generally means a suspension of particles dispersed in air or gas. "Autonomous" diagnostic systems and methods mean generating a diagnostic test result "with no or minimal intervention by a medical professional." The U.S. FDA classifies medical devices based on the risks associated with the device and by evaluating the amount of regulation that provides a reasonable assurance of the device's safety and effectiveness. Devices are classified into one of three regulatory classes: class I, class II, or class III. Class I includes devices with the lowest risk and Class III includes those with the greatest risk. All classes of devices as subject to General Controls. General Controls are the baseline requirements of the Food, Drug and Cosmetic (FD&C) Act that apply to all medical devices. In vitro diagnostic products are those reagents, instruments, and systems intended for use in diagnosis of disease or other conditions, including a determination of the state of health, in order to cure, mitigate, treat, or prevent disease or its sequelae. Such products are intended for use in the collection, preparation, and examination of specimens taken from the human body. The exemplary devices disclosed herein can operate and produce a high-confidence result autonomously, and consequently, has the potential to be regulated as a Class I device. In some regions of the world with high burdens of TB infection, access to medically trained personnel is very limited. An autonomous diagnostic system is preferred to one that is not autonomous.

The terms "a" or "an" are used to include one or more than one, and the term "or" is used to refer to a nonexclusive "or" unless otherwise indicated. In addition, it is to be understood that the phraseology or terminology employed herein, and not otherwise defined, is for the purpose of description only and not of limitation. Unless otherwise specified in this disclosure, for construing the scope of the term "about," the error bounds associated with the values (dimensions, operating conditions etc.) disclosed is ±10% of the values indicated in this disclosure. The error bounds associated with the values disclosed as percentages is ±1% of the percentages indicated. The word "substantially" used before a specific word includes the meanings "considerable in extent to that which is specified," and "largely but not wholly that which is specified."

DETAILED DISCLOSURE

Particular aspects of the invention are described below in considerable detail for the purpose for illustrating the compositions, and principles, and operations of the disclosed methods and systems. However, various modifications may be made, and the scope of the invention is not limited to the exemplary aspects described.

An exemplary diagnosis system 100 based on exhaled breath analysis ("EBA") may comprise an EBA sample collection subsystem 101, and an analysis subsystem system 102 (FIGS. 1-3). These two subsystems are described in detail below.

EBA Sample Collection Subsystem 101

Subsystem 101 may comprise sample extraction component 104 which may be in the form of at least one of a shroud, and a loose-fitting cone shaped device. A tight-fitting suitable mask suitable for receiving an individual's face or that may be removably attached using straps and the like to the face/head of a patient/individual 105 may also be used but is not preferred because it is difficult to ensure a good fit on all humans, especially men with beards/facial hair. The individual may sit in an optional containment booth 106 to isolate the patient's EBA from the ambient air in the testing room or area. An exemplary containment booth 106 may comprise a modified pulmonary function test body box as sold by Morgan Scientific Inc. (Haverhill, MA) by replacing the plethysmograph components with the extraction component 104 described herein such that booth 106 is in fluid communication with extraction component 104. Booth 106 may also be a modified version of the Respiratory Aerosol Sampling Chamber (RASC) chamber described by Wood et al. (2016) and may incorporate the features and capabilities described therein. The disclosure of Wood et al. (2016), a non-patent literature cited in the Reference section, is incorporated by reference herein in its entirety. In the RASC chamber, a participant is seated and engages passively in an exhaled air sampling protocol. Approximately an hour is spent in the chamber following the phases outlined in Wood et al. Briefly, the chamber is sealed, and an air purge phase is performed entraining ambient air through high-efficiency particulate arrestance (HEPA) filters for a period of 10 minutes. This was followed by a participant-driven contamination phase in which the chamber is isolated from the external environment and the proportion of exhaled air is allowed to rise to a 10% threshold defined by a chamber $CO_2$ concentration of 4,000 ppm above the ambient level (based on an assumed exhaled air $CO_2$ concentration of 40,000 ppm). Measured $CO_2$ may be used to calculate exhaled air volume as described in Wood et al. If the target is not reached after 30 minutes have elapsed, the sampling phase is started at a lower exhaled air proportion. After sampling, the chamber is again purged to remove residual Mtb from the air. Contamination of the sampling chamber was driven primarily by tidal breathing in addition to spontaneous coughing or sneezing. Particles and organisms derived from sources other than breath were minimized by the participant wearing a full-body DuPont Tyvek suit during sampling and an initial purge phase to minimize ambient contamination. Component 104 serves to extract the aerosol particles emitted though the mouth and nose of patient 105 into a stream of air that acts as a sheath fluid (normally air) supplied from air source 107, which assists in transporting the aerosol toward the exit of component 104, and into sample capture component 108 without depositing on the walls of component 104. Air source 107 may be an air pump or compressor. Examples of 104 are the funnel-shaped cone used by Milton's group or the face mask used by Fennelly. The air sheath fluid may be added though the walls or at the large rim of the component 104, or more generally into the booth 106. The air flow fed to component 104 may be suitably filtered (e.g., using a HEPA filter) to remove all or nearly all particulate matter, including, but not limited to dust and fomites, in ambient air. (HEPA, which stands for High Efficiency Particulate Air), is a designation used to describe filters that are able to trap 99.97 percent of particles that are 0.3 microns and is used to remove all or nearly all particulate matter, including, but not limited to dust and soot, in ambient air. Further, the sheath fluid flow may be humidified to enable EBA particle size growth, thereby enabling a large fraction of the particles in the breath to be captured downstream in the aerosol capture device 108. Interface tubing 109 fluidly connects extraction component 104 to sample capture component 108 and may be further chilled to enable the EBA particles to grow in size. Chilling may be provided using a refrigeration system or more preferably using Peltier thermoelectric cooling devices 113 that are small, lightweight and consume less power to operate. A Peltier cooling device, for example, as supplied by Marlow Industries (Dallas, TX), TE Technologies Inc. (Traverse City, MI), generally comprises an array of alternating n- and p-type semiconductors. The array is soldered between two ceramic plates, electrically in series and thermally in parallel. Bismuth telluride, antimony telluride, and bismuth selenide are the preferred materials for Peltier effect devices because they provide the best performance from 180 K to 400 K and can be made both n-type and p-type. Peltier effect creates a temperature difference by transferring heat between two electrical junctions when a voltage is applied across joined alternating n- and p-type semiconductors to create an electric current. Heat is removed at one junction and cooling occurs. Heat is deposited at the other junction and is readily removed with a fan or blower.

Component 104 may be disposable to limit the risk of a patient becoming contaminated or infected with a pathogen emitted by a previous patient. Alternatively, component 104 may be reusable, in which case it may be sterilized using sterilization component 110 using at least one of a disinfecting spray rinse produced using a suitable nebulizer, UV radiation, peroxide solution or vapor treatment, steam sterilization, or a combination thereof. A nebulizer, such as a Collison-type nebulizer (supplied by CH Technologies), may be fluidly connected near the exhaust of the cone, that is, near the throat region 111. A rinse fluid is nebulized to disinfect the extraction component 104, tubing 109 and capture component 108. The rinse fluid is selected to ensure that the EBA and condensed EBA (exhaled breath condensate) samples and the components in sampling subsystem 101 remains in a generally sterile condition. For example, if 70% ethanol in isopropyl alcohol is used, this disinfectant solution may be readily removed from the sample by evaporation and does not interfere with the analysis. Sterilization component 110 (e.g., nebulizer) may be activated briefly at the end of a sample collection period to provide a final rinse of the inlet tubing 109 and capture component 108. Nebulizer 110 may again be activated to clean the sample extraction component 108 prior to the reuse by the next patient. Waste fluid may be pumped using pump 116 to a waste receptable by switching the valve 117 to fluidly connect pump 116 to the waste receptacle. Although the exemplary sample extraction component 104 and sample capture component 108 may be disinfected between patients, exemplary system 100 with MS diagnostic devices do not require 100% decontamination of the exemplary systems between different individuals because of the high sensitivity to bioaerosol fragments of interest even in the presence of trace contaminants.

Although extraction component 104 and tubing 109 is shown to be converging/diverging in diameter, the diameter of the tubing may be the same as the diameter of throat 111 of component 104 or may be larger or smaller than the diameter throat 111. Sensors 112 include, but are not limited to, a $CO_2$ sensor and a particle sizer/counter, and may be fluidly connected to component 104 near throat region 111. Sensors 112 provide an indication of the volume of exhaled breath that has been sampled. Continuous $CO_2$ monitoring allows for a close approximation of the proportion of exhaled air volume for each participant in the containment booth 106 at any given time. For example, for a person with reduced lung capacity, and having relatively small forced vital capacity (FVC), for example, less than two liters, or a weak cough, for example, less than 1 liter of exhaled breath, the patient may automatically, and in real-time be instructed to provide more FVC breaths or coughs until a sufficient volume of exhaled breath aerosol has been collected. Wurie (2016) describes bioaerosol production by patients with tuberculosis during normal tidal breathing and implications for transmission risk. Optical particle counter technology was used to measure aerosol size and concentration in exhaled air (range 0.3-20 µm in diameter) during 15 tidal breaths across four groups over time: healthy/uninfected, healthy/Mtb-infected, patients with extra-thoracic TB and patients with intrathoracic TB. High-particle production was defined as any 1-5 µm sized bioaerosol count above the median count among all participants (median count=2 counts/L). Data from 188 participants were obtained pre-treatment (baseline). Bioaerosol production varied considerably between individuals. Multivariable analysis showed intrathoracic TB was associated with a 3½-fold increase in odds of high production of 1-5 mm bioaerosols compared with healthy/uninfected individuals. Wurie (2016), a non-patent literature cited in the Reference section is incorporated by reference herein in its entirety.

EBA sample capture component 108 may be a wetted wall cyclone (as shown in FIG. 2), one or more impactors (for example, as is demonstrated by Milton), or an impinger, that use dry or nearly-dry collection methods following by wash resulting in a resuspension of the EBA particles from the collection surface of the cyclone. Exemplary capture component 108 includes, but is not limited to, wetted-film impactors (McDevitt, 2013), Coriolis™ wetted-wall cyclone (Bertin, France), impingers such as the BioSampler (SKC, Inc, Eight Four, PA), impaction-based devices such as the BioCapture (FLIR Systems, OR), and 300 L/min wetted wall cyclone (King, 2012), and the BioSpot Sampler (Aerosol Devices, Fort Collins, CO). McDevitt's wetted film impactors and the BioSpot Sampler use a combination of humidification and condensation to "grow" the size of the aerosol particles, thereby enhancing the collection efficiency of submicron-sized particles in EBA. Each of the non-patent literature and contents therein published by McDevitt and King as cited in the Reference section is incorporated by reference herein in their entirety. EBA aerosol particles may be collected directly into a liquid or may be collected on a filter medium and extracted by backflushing water or solvent through the filter, using a dissolvable filter material and dissolving the filter, or pulverizing the filter in a liquid, and then analyzing the resulting slurry. EBA aerosol particles may be collected by impacting the particles onto a dry surface and then washing the particles from the surface with a suitable fluid. Virtual impactors may be used to concentrate aerosols of a certain "cut size," and those larger than the cut size. Virtual impactors, such as those described in U.S. Pat. No. 6,062,392, can be combined with impactors and other devices to increase the inlet air flow rate of air containing the exhaled breath as shown in U.S. Pat. No. 6,267,016. Sample capture component 108 may include condensation growth tubes to grow submicron particles into micron sized particles. Biomarkers may include lipids from Mtb cell walls, and these lipids may be used in disease diagnosis in addition to Mtb cells. Close to 100% of the exhaled sample is collected. There is no need to dilute the sample 115 collected with saline solution.

EBA aerosol particle capture component 108 may have a flow rate sheath fluid (air) of between about 100 L/min and about 1000 L/min. The air flow rate is preferably more than 200 L/min and is about 300 L/min. McDevitt used flow rates of 130 L/min which is not sufficient to capture EBA produced during coughing reliably. The high flow rates minimize loss of aerosol due to blow-back during cough maneuvers. Higher flow rates lead to more entrainment of the EBA particles. Preferably, the aerosol capture component 108 collects the particles into a small volume of condensed sample 115, and therefore produces concentrated aerosol biomass (for example, at least 1 nanoliter of peripheral lung fluid per ml of collection fluid). Sample 115 may be transferred to the analysis subsystem 102 using a pump 116, which is preferably a peristaltic pump. Valve 116 may be used to either route the condensed sample 115 to the analysis subsystem 102 or to a waste receptacle, for example, during decontamination of sample collection system 101. The volume of EBA sample fluid of less than about 1 ml is preferred and targeted. The exemplary disclosed system may be capable of and producing between about 100 microliter and about 200 microliter of fluid. Therefore, not all of the exemplary EBA sample capture components as identified herein are preferred for use in the disclosed exemplary sample collection subsystem 101 for an autonomous system. For example, the BioSampler and Coriolis aerosol sampler collect EBA aerosol particles into aqueous samples that are greater than 10 ml in volume. This large volume results in a very dilute sample, and a particle concentration method is needed. A preferable aerosol capture component 108 would have high inlet air flow rate to entrain a large fraction of the particles in exhaled breath, even during a cough a sneeze flow rate of exhaled breath is very uneven in time. Similarly, McDevitt's wetted film impactor uses an injection of steam upstream of the impactor which is then condensed to provides samples that are collected into 50 ml centrifuge tubes, and then concentrated using a centrifuge. As previously described, the exemplary EBA sample collection subsystem will capture particles in a liquid volume that is about 1 ml or less. Similar to chilling tubing 109 that fluidly connects extraction component 104 to component 108 using Peltier devices, component 108 is preferably chilled using one or more Peltier cooling devices 114 to enable the EBA particles in the exhaled breath to grow in size. articles formed deep in the lungs may be on the order of 100 microns in diameter but can be grown to greater than 1 micron. The chilling of component 108 and tubing 109 facilitates condensation of volatile compounds in the exhaled breath which are also collected in the liquid sample. The exemplary EBA capture component 108 therefore collects both volatile and non-volatile biomass in exhaled breath. When a cyclone is used as capture component 108, the cyclone and the cyclone inlet tubing are preferably made of copper, copper alloys such as the nickel-copper Alloy 400 or other alloys having high thermal conductivity and low cost. Further copper and copper alloys have inherent antimicrobial properties. Peltier cooling devices 113 and 114 are preferred as chilling devices due to the ease and accuracy with which they can control the temperature of the cyclone inlet 109 and the body of cyclone 108. Entrainment air fed into sample capture component 108 (for example, when 108 is a cyclone) may be supplied using pump 118 and filtered using HEPA filter 119.

EBA Sample Analysis Subsystem 102

EBA liquid sample 115 comprising EBA aerosol particles is then routed to sample processing component 120 for analysis using at least one of a diagnostic device 121 for analyzing EBA particles, and device 122 for analyzing volatile organics in exhaled breath. Sample processing component 120 may comprise elements necessary to perform one or more of the following steps:

(a) Sample 115 may be placed in a cup or vial. For example, the Series 110A Spot Sampler (Aerosol Devices) uses 32 well plates with circular well shape (75 μL well volume) or teardrop well shape (120 μL well volume) which are heated to evaporate the excess fluid/liquid in the sample to concentrate the sample.

(b) Sample 115 may be placed in a cup and exposed to a source of vacuum to cause the fluid to evaporate to concentrate the sample.

(c) Sample 115 may be mixed with a high volatility solvent (for example, methanol, ethanol, and acetonitrile) to accelerate the evaporative process.

(d) Sample 115 may be subjected to a bead-based extraction. Bead based extraction may be used to extract biomarkers from a dilute solution. For example, a micron sized magnetic bead may be coated with a glycan material that binds well with protein biomarkers such as EBA particles. The beads may be intimately mixed with the EBA sample by an oscillating magnetic field. After a period of mixing, the beads may be pulled to one side with a constant magnetic field, and then released into a small volume of solvent to extract the EBA particles as a concentrated sample.

(e) Sample 115 may be subjected to a solvent extraction process whereby the sample is intimately contacted with an immiscible fluid such that the biomarkers (EBA particles) are preferentially transferred to the immiscible fluid. For example, a relatively large aqueous collection fluid sample (>1 ml) may be contacted with a relatively smaller volume of organic solvent (for example, hexane or chloroform), transferring lipids from EBA particles and cell fragments in the sample to the organic phase.

Many diagnostic devices may be adapted for use in analysis subsystem 102, that include, but are not limited to devices that perform genomics-based assays (such as PCR, rt-PCR and whole genome sequencing), biomarker recognition assays (such as ELISA), and spectral analysis such a mass spectrometry (MS). Of these diagnostic devices, MS is preferable on account of its speed of analysis. The MS techniques that are preferable for biomarker identification are electrospray ionization (ESI) and matrix assisted laser desorption ionization (MALDI) MS. ESI may be coupled to high resolution mass spectrometers such as the Oribtrap (ThermoFisher) ESI-MS devices are typically very large and heavy, and require a high level of expertise to operate, and are not suitable for autonomous operation or applications such as point of care diagnostics. In contrast, MALDI-MS devices may be compact, lightweight, consume less than 100 watts of power and provide sample analysis in less than 15 minutes. MALDI-MS is a preferred diagnostic device for point-of-care diagnostics suitable for ACF. Including time for sample preparation, the analysis time using MS may be less than about 15 minutes. The sample must be dry before it is inserted into the MALDI spectrometer, and large (>1 ml) samples cannot be dried quickly without analyte loss or degradation. With a concentrated sample 115, sample analysis using a MALDI MS may be less than 5 minutes (including the sample preparation) because less time is needed to evaporate the water from the sample.

In "matrix assisted laser desorption ionization" (MALDI), large molecules may be analyzed intact using mass spectrometry. In this technique, the target particle (analyte) is coated by a matrix chemical, which preferentially absorbs light (often ultraviolet wavelengths) from a laser. In the absence of the matrix, the biological molecules would decompose by pyrolysis when exposed to a laser beam in a mass spectrometer. The matrix chemical also transfers charge to the vaporized molecules, creating ions that are then accelerated down a flight tube by the electric field. Microbiology and proteomics have become major application areas for mass spectrometry; examples include the identification of bacteria, discovering chemical structures, and deriving protein functions. MALDI-MS has also been used for lipid profiling of algae. During MALDI-MS, a liquid, usually comprised of an acid, such as tri-fluoro-acetic acid (TFA), and a MALDI matrix chemical such as alpha-Cyano-4-hydroxycinnamic acid, is dissolved in a solvent and added to the sample. Solvents include acetonitrile, water, ethanol, and acetone. TFA is normally added to suppress the influence of salt impurities on the mass spectrum of the sample. Water enables hydrophilic proteins to dissolve, and acetonitrile enables the hydrophobic proteins to dissolve. The MALDI matrix solution is spotted on to the sample on a MALDI plate to yield a uniform homogenous layer of MALDI matrix material on the sample. The solvents vaporize, leaving only the recrystallized matrix with the sample spread through the matrix crystals. The acid partially degrades the cell membrane of the sample making the proteins available for ionization and analysis in an MS. Other MALDI matrix materials include 3,5-dimethoxy-4-hydroxycinnamic acid (sinapinic acid), α-cyano-4-hydroxy-cinnamic acid (α-cyano or α-matrix) and 2,5-dihydroxyben-zoic acid (DHB) as described in U.S. Pat. No. 8,409,870.

In exemplary system 100, the use of chillers to chill the capture component 108 and inlet line 109 produces sample 115 which comprises condensed volatile organic compounds in exhaled breath and cooled liquid sample comprising EBA. Therefore, sample 115 may be routed to diagnostic devices 122 to analyze condensed volatile organics and to device 121 to analyze non-volatile EBA particles. During sample processing in step 204 (FIG. 5), the liquid sample 115 may be warmed using a heater, driving of the volatile compounds into a diagnostic device 122 such as GC-MS, GC-IMS, volatile ion chromatography, or any other type of analysis method suitable for analyzing volatile organic compounds. FIG. 4 shows that that ion chromatograms from exhaled breath may be used to differentiate between healthy individuals and TB-infected patients. Hashoul (2019) discloses use of sensors for detecting pulmonary diseases including TB from exhaled breath. Hashoul describes breath analysis of 226 symptomatic high-risk patients using GC (gas chromatography)-MS, pointing out several biomarkers of active pulmonary TB. They suggested biomarkers in oxidative stress products, such as alkanes and alkane derivatives, and volatile metabolites of *Mycobacterium tuberculosis*, such as cyclohexane and benzene derivatives. Their results differentiated between positive and negative TB with 85% overall accuracy, 84% sensitivity and 64.7% specificity, using C-statistic values. Metal oxide sensors used. Moreover, the sensors array had a sensitivity of 93.5% and a specificity of 85.3% in discriminating healthy controls from patients with TB, and a sensitivity of 76.5% and specificity of 87.2% in identifying patients with TB within the entire test population. The use of gold nanoparticle (GNP) and QMB (quartz microbalance sensors) were also discussed. The non-patent literature published by Hashoul cited in the Reference section is incorporated herein in its entirety. If chilling is not employed in subsystem 101 as described above, liquid sample 115 may not contain any condensed volatile organics. As a result, diagnostic device may be limited to analysis of EBA particles in the liquid using device 121.

FIG. 5 is a schematic diagram of an exemplary diagnostic method 200 using an exemplary system 100 as previously disclosed herein. Exemplary method 200 may be used to perform autonomous point-of-care diagnosis based on exhaled breath. In step 201, the individual 105 may directed to be seated; the chair may optionally be located in containment booth 106. In step 202, extraction component 104 may be removably fitted to the individual's head or a cone that is larger than the head is positioned to fit loosely around the individual's head. Sample capture component 108 is activated which causes air to be drawn around the patient's head and into the sample capture device. When a cyclone is used as sample capture component 108 air flow to component 108 and chilling of the cyclone body and inlet tubing 109 are initiated. Preferably filtered sheath air is supplied to component 104. Sheath air may be humidified, preferably to greater than 90% relative humidity. Individual 105 is then instructed to perform one or more predetermined maneuvers 203 which may include a pre-set number of repetitions. The maneuvers may include performing one or more FVC or modified FVC maneuvers for generating EBA samples from the lower respiratory tract, producing one or more cough samples for generating EBA predominately from the upper respiratory tract, and producing one or more sneeze samples that generates EBA predominately from the nasal passages/upper respiratory tract. A modified FVC is an FVC preceded by a deep exhale followed by a 5 to 10 second pause. This exhale and pause cause bronchiole closure, followed by its reopening during the FVC inhalation. The closing and reopening of the small lung passages including the alveoli is believed to result in increased particle production. For TB diagnosis using exemplary system 100, between about 3 to about 5 modified FCV repetitions may be needed. A maneuver may include a coughing, FVC breathing, modified FVC breathing and sneezing. For diagnosis of some other diseases all maneuvers may be needed. Sneezing may be induced by injecting a small dose of pepper or other spices in aerosol form into the nasal passages. Preferably, at least three modified FVC breaths for sampling the lower respiratory tract, and a series of coughs for sampling the upper respiratory tract may be needed. The lower respiratory tract generally comprises the trachea, the lungs, and all segments of the bronchial tree (including the alveoli), and the organs of the lower respiratory tract are located inside the chest cavity. The upper respiratory tract generally comprises the nose, the pharynx, and the larynx, and the organs of the upper respiratory tract are located outside the chest cavity. In some case, at least ten modified FVC breaths may be needed. A series of sneezes may be induced to sample the nasal passages. A preferred modified FVC that increases biomass collection per breath is one where the patient first exhales, then pauses for up to 10 seconds prior to a FVC inhale, followed by a complete exhale as disclosed by Bake et al. (2019), a non-patent literature cited in the Reference section, which is incorporated by reference herein in its entirety. A preferable breath maneuver may comprise 10× cough/FVC/bronchial blast. Instead of a cone or shroud, sample extraction 104 component may include continuous positive airway pressure (CPAP) masks (e.g., Dreamware and Amara masks sold by Philips Respironics) that are used for treating sleep apnea. CPAP works by blowing air into the throat via a mask, subtly increasing air pressure in the throat and preventing the airway from narrowing but is modified to collect exhaled breath from various breath maneuvers using a flow of air as the sheath fluid.

The patient is then instructed to leave the chair and to be seated in the waiting area. The extraction component 104 may be disinfected in UV light. In sample processing step 204, sample 115 is automatically transferred from collection subsystem 101 for sample processing in analysis subsystem 102. The type of sample processing depends on the type of diagnostic device. When the diagnostic device is MALDI-MS, sample processing may comprise the steps of plating the sample 115 on to a MALDI-MS sample disk using a peristaltic pump, heating the disk to concentrate the sample, adding the MALDI matrix/acid/solvent (described below) and drying the disk. The sample disk is then analyzed using a MALDI-MS in step 205. The spectrum obtained is compared to spectra from samples that were known positives to specific respiratory infections, and also to spectra of samples form patients know to be healthy, and a diagnosis of the patient is generated. The result may then be communicated to a clinician or to the patient. Once the extraction component 204 is attached to the patient, and sample extraction is initiated, the exemplary method is autonomous (with the exception of asking the patient to the leave the chair) after performing the required maneuvers and generates a test result of the diagnosis.

Regarding FVC maneuvers in step 203, FIGS. 6A-C shows the normal variability of breath aerosol from healthy individuals for 10 repetitions of the FVC breath maneuver. Even for health individuals, the variability in the amount and particle size distribution of exhaled breath aerosol is very large. The data were captured using a LASEX II (PMS, City, CO). A similar variability was also notice during EBA collection from cough maneuvers. Particle size distributions help to determine the total exhaled particle mass by integrating the particle size distribution over time. This aspect helps to determine if the sample collected is sufficient for analysis. FIG. 7 shows the carbon dioxide measurements in exhaled breath during bronchiole film burst (BB), FCV and cough maneuvers. A strong correlation was observed by Patterson et al. between $CO_2$ production rate and aerosol particle production. Measured $CO_2$ may be also used to calculate exhaled air volume as described in Wood et al.

FIG. 8 shows the volume (nanoliters) of exhaled breath fluid volume based on particle size distribution and particle concentrations as measured by the LASEX instrument. If the preferred method is the method that provides the largest sample, the modified FVC maneuver is preferred over standard FVC. Cough provides a similar amount of EBA sample volume, predominantly from the upper respiratory tract. Both of these methods produce sufficient sample to detect TB infection in patients otherwise known to be infected, but who are not yet on treatment.

Regarding the use of MS for detecting biomarkers for TB infection in exhaled breath, positive and negative ion signals containing 1000s of features were obtained (or extracted) using a high resolution Orbitrap mass spectrometer (ThermoFisher Scientific) from samples collected from TB-patients (n=20), and non-TB/control samples (n=13). Masses above a 5:1 signal to noise ratio (SNR) were selected. Weighted principal components analysis (PCA), an unsupervised dimensionality-reduction algorithm, was used to reduce the large set of signals to two components. PCA provided 2-D visualization, which was used to explore whether extracted signals would reveal intrinsic differences between two classes of samples, TB and non-TB. PCA results (FIG. 9) revealed that the samples of each group were prone to cluster together, suggesting extracted signals collected from high-resolution mass spectrometry could be used to distinguish between the two classes of samples.

The exemplary systems and methods described herein are not necessarily limited in their diagnostic capability to respiratory infections. Lung cancer, for example, may also release biomarkers into the peripheral lung fluid, and these biomarkers would be readily detected by the systems and methods disclosed. Furthermore, because blood comes into intimate contact with the alveolar lining in the lungs, biomarkers of infection and cancer in other parts of the body (beyond the lungs) may be transferred across the alveolar lining and into the peripheral lung fluid, and thus, may be detected by the analysis of EBA. As a result, the scope of the invention is not limited to the detection and diagnosis of respiratory diseases.

An exemplary sample extraction component may comprise a packed bed column to selectively capture the non-volatile organic components including EBA particles in exhaled breath. The non-volatile components in exhaled breath may comprise breath aerosol particles comprising at least one of microbes, virus, metabolite biomarkers, lipid biomarkers, and proteomic biomarkers characteristic of the respiratory disease. The packed bed column may comprise solid particles comprising at least one of resins, cellulose, silica, agarose, and hydrated $Fe_3O_4$ nanoparticles. The packed bed column may comprise resin beads having octadecyl acrylate (C18) functional groups on the surface. The resin beads may have a nominal diameter of between about 12 μm and about 20 μm. The solid particles may comprise functional groups immobilized on the surface of the particles wherein the functional groups comprise at least one of C18 (octadecyl), octyl, ethyl, cyclohexyl, phenyl, cyanopropyl, aminopropyl, 2,3-dihydroxypropoxypropyl, trimethyl-aminopropyl, carboxypropyl, benzenesulfonic acid, propylsulfonic acid, an ion exchange phase, a polymer phase, antibodies, glycans, lipids, DNA and RNA. The ion exchange phase may comprise at least one of diethylaminoethyl cellulose, QAE Sephadex, Q sepharose, and carboxymethyl cellulose. The polymer phase comprises at least one of polystyrene-co-1,4-divinylbenzene, methacrylates, polyvinyl alcohol, starch, and agarose. The antibodies may comprise at least one of anti-human albumin, anti-Influenza A virus NP and Anti-SARS-CoV-2 virus. The antibodies may be immobilized on protein A/G agarose beads. The capture element may be cooled to a temperature at or below ambient temperature. Commonly owned International Pat. Appl. No. PCT/US20/48035 titled "DIAGNOSIS OF RESPIRATORY DISEASES USING ANALYSIS OF EXHALED BREATH AND AEROSOLS," provides additional details related to exemplary sample extraction components comprising a packed bed column and is incorporated by reference herein in its entirety.

Lipid extraction may be conducted using classic Folch solvent separation method and an EBA sample collected into a buffer solution, such as phosphate-buffered saline, may require overnight lyophilization and centrifugation. Disclosed is an exemplary system 190 for diagnosis of respiratory diseases in an individual using exhaled breath, the system comprising a sample collection system comprising a sample extraction component 104 configured to receive an individual's face for extracting breath aerosol (EBA) particles expelled from the individual during a predetermined number of breath maneuvers into a flow of air fed into the extraction component, a sample capture component comprising means to collect the EBA particles into a collected liquid sample 115 and a packed bed column 161 to selectively capture the EBA particles from the collected liquid sample onto the packed bed, means to elute the collected EBA particles from the packed bed using one or more solvents, and a diagnostic device for analyzing the EBA particles comprised in the one or more solvents. The flow rate of air entering the sample capture component may be between about 50 L/min and about 500 L/min. The volume of the collected sample 115 may be between about 100 microliter and about 10 ml. The means to collect the EBA particles may comprise at least one air pump 107, 118, and an impactor 108 wherein the at least one air pump provides the flow of air to carry the exhaled breath from the extraction component into the impactor and wherein the impactor separates the EBA particles from exhaled breath to produce the collected sample 115. Impactor 108 may comprise at least one of a cyclone, a wetted wall cyclone, one or more wetted film impactors, a virtual impactor, and an impinger. Sample extraction 104 component may comprise at least one of a cone shaped device, a shroud, CPR rescue mask, a CPAP mask, a ventilator mask, and a medical universal mouthpiece. The diagnostic device may comprise at least one of PCR, rt-PCR, immuno-based assay, mass spectrometer (MS), MALDI-MS, ESI-MS, GC-MS, GC-IMS and MALDI-TOFMS. One or more chilling devices 114 may be configured to be in thermal communication with the walls of impactor 108 collect the EBA particles. Impactor 108 may be chilled to a temperature greater than about 0° C. and less than about 10° C. using the one or more chilling devices. Impactor 108 may be chilled to a temperature greater than about 0° C. and less than about 4° C. using the one or more chilling devices. The collected sample 115 may be transferred to packed bed column 161 using at least one of a manually operated syringe, a dispensing pump and a robotic sample transfer system. Packed bed column 161 may comprise solid particles comprising at least one of resins, cellulose, silica, agarose, and hydrated $Fe_3O_4$ nanoparticles. Packed bed column 161 may comprise resin beads having C18 functional groups on the surface. The resin beads may have a nominal diameter of between about 12 μm and about 20 μm. The weight of the backed packed bed may be about 25 mg. The means to elute the collected EBA particles from the packed bed may comprise at least one of one or more syringes, and one or more pumps. The one or more solvents may comprise at least one of acetonitrile, methanol, acid, isopropanol, the remaining being water.

In an exemplary packed bed column 161 comprising C18 resin beads of nominal diameter of between about 12 μm and about 20 μm, the resin beads may be packed between two porous polymeric frit discs. The polymeric frit disc disposed at the inlet end of the packed column may be characterized by average pore size of at least 35 μm. The polymeric frit disc disposed at the outlet end of the packed column may be characterized by average pore size of about 10 μm.

Disclosed is an exemplary method for diagnosing respiratory diseases in an individual using exhaled breath, the method comprising extracting EBA particles expelled from the individual during a predetermined number of breath maneuvers into a flow of air fed into a sample extraction component 104 configured to receive an individual's face, collecting the EBA particles from exhaled breath and air as a collected liquid sample 115, capturing the EBA particles in the collected liquid sample using a packed bed column 161 to selectively capture the EBA particles from the collected liquid sample onto the packed bed, eluting the collected EBA particles from the packed bed using one or more solvents and, analyzing the EBA particles comprised in the one or more solvents using a suitable diagnostic or analytical device. The one or more solvents may comprise at least one of acetonitrile, methanol, acid, isopropanol, the remaining being water. The one or more solvents may comprise between about 50 vol.-% and about 70 vol. % acetonitrile in water. The one or more solvents may comprise between about 50 vol.-% and about 70 vol. % isopropanol in water. EBA samples in the collected liquid sample may be loaded directly onto the column by any suitable means, for example, by flushing or washing the column with the collected liquid sample comprising EBA biomarkers. After the washing step, metabolite molecules and proteins, which are less nonpolar, may be eluted using suitable solvents, for example, using acetonitrile in a first stage extraction step. In a second stage extraction step, lipids, which are nonpolar, may be eluted using suitable solvents, for example, using 2-isopropyl alcohol. EBA sample extraction using the exemplary packed bed column is rapid, as the two-stage separation process may be completed in about 3 min. per sample, and the use of an extraction bed in cartridge form is amenable to automation. As described in the Example provided herein, the exemplary dual-mobile phase extraction method enabled extraction of both small metabolites and lipids from the same EBA sample collected from multiple subjects for tuberculosis detection. The EBA sample in a buffer solution (collected liquid sample) may comprise metabolites, protein, and lipid biomarkers and any whole pathogens.

The exemplary systems and methods disclosed herein may comprise robotic systems and components. For example, the systems and methods may comprise a robotic sample transfer system to spot a collected sample on a sample plate and conduct further processing or sample treatment, and analysis of the treated sample. Commonly owned International Pat. Appl. No. PCT/US20/48042 titled "SYSTEMS AND METHODS OF RAPID AND AUTONOMOUS DETECTION OF AEROSOL PARTICLES," provides additional details related to exemplary robotic sample transfer systems is incorporated by reference herein in its entirety. A collected sample need not be spotted on a sample plate prior to processing and analysis. For example, EBA particles in a collected liquid sample may be aerosolized using a nebulizer and coated "on-the-fly" using a MALDI matrix to form coated aerosol EBA particles. The coated particles may be analyzed using aerosol time of flight mass spectrometry (ATOFMS). "On-the-fly" means that the particles comprising the aerosol are not collected onto a surface (for example, onto the surface of a MALDI plate) or into a liquid as a step in the coating process. Commonly owned U.S. patent application Ser. No. 15/755,063 titled "COATING OF AEROSOL PARTICLES USING AN ACOUSTIC COATER," provides additional details and is incorporated by reference herein in its entirety.

EXAMPLE

200 EBA samples were collected from 99 study subjects during different visits related to a clinical trial. Active TB cases were defined as study subjects who tested positive ("GXP positive") during analysis of their sputum using a GeneXpert MTB/RIF system (Cepheid, Sunnyvale, CA). Subjects who tested negative with the same method ("GXP negative") were used as the control group. 73 subjects were found to be GXP negative and 26 subjects were found to be GXP positive. EBA samples from these subjects were also collected in about 10 ml buffer solution using exemplary system 190 (FIG. 10). EBA samples from each subject were extracted from the buffer solutions using a C18 packed bed column.

C18 beads of nominal diameter of 20 μm (Hamilton, Reno, NV) were packed into a packed bed column. About 10 ml of buffer solution comprising the EBA sample was loaded into the column using a syringe pump by flushing. The column was washed first with about 400 μL of 0.1% FA in water three times for cleaning and desalting prior to loading. The column was then flushed using 400 μL of 50% acetonitrile (ACN) in water to elute metabolites and proteins. After the first-stage extraction, the column was eluted using 400 μL of 70% isopropyl alcohol (IPA) to extract lipids. The extracted samples were lyophilized overnight. For metabolite analysis using mass spectrometry, dried samples were resuspended in 0.05% TFA in water. For lipid analysis using mass spectrometry, dried samples were suspended in 50% ACN. Samples containing MS-grade water were used as negative control samples. For quality control, a mixture of short peptides was used to monitor retention time, mass resolution and accuracy.

Figure 11C:
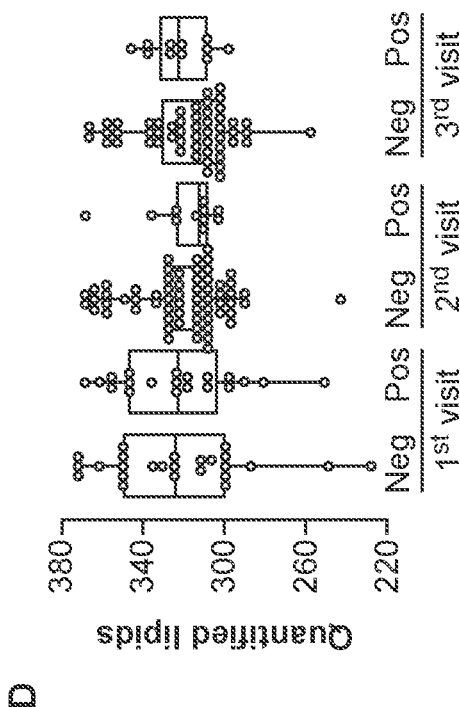
Figure 11D:
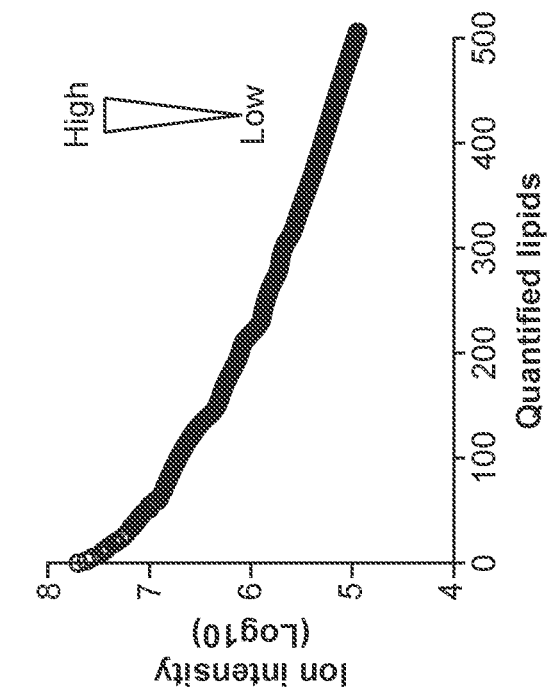
Figure 11E:
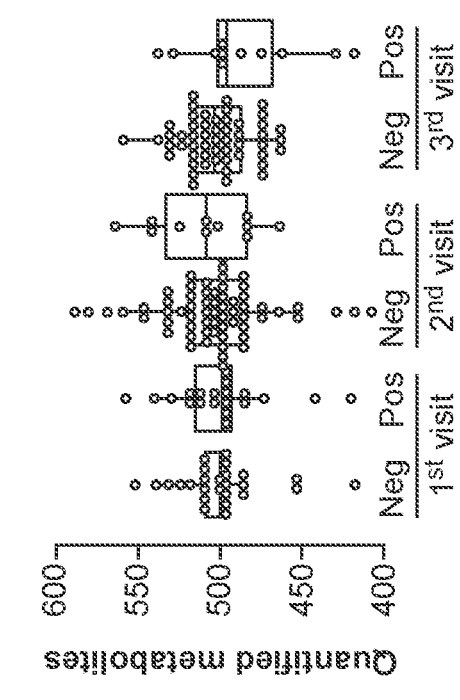
Figure 11F:
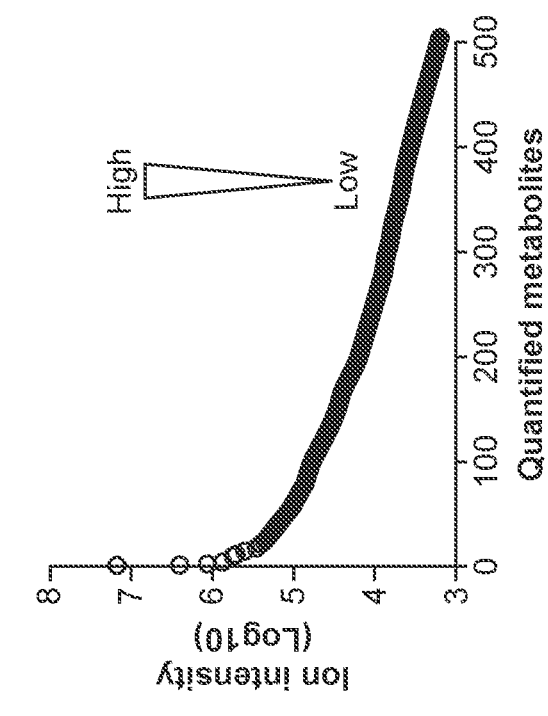

For nano-liquid chromatography and mass spectrometry, metabolite and lipid samples were centrifuged at 10,000 g for 10 min. before being processed using an autosampler in an EASY-nLC 1000 system and characterized using a LTQ orbitrap system in positive ion mode (Thermo Fisher Scientific). Chromatograms were generated using an Acclaim PepMap 100 C18 trap column (0.2 mm×20 mm, 5 μl/min) and an analytical column (75 μm×150 mm, 300 nL/min). The mobile phase for metabolites was 80% ACN prepared in 0.1% FA with water from 5% to 70% in 60 min. The mobile phase for lipids was 90% IPA and 10% ACN from 5% to 90% in 60 min. For accurate mass measurement, the mass spectrometry resolution was set to 30,000. High energy collision-induced disassociation was used for ion fragmentation with 35% total energy. The total ion chromatogram of extracted small metabolites and lipids in EBA sample showed that EBA samples produced clear molecule signals compared to blank samples (FIG. 11A). Representative total ion chromatogram of small metabolites in EBA samples of GXP positive and GXP negative subjects showed no obvious differences between the two groups (FIG. 11B), suggesting that deeper analysis using more sensitive analytical methods (as described below) may be required to distinguish between the two groups. As shown in FIGS. 11C-D, about 500 features were extracted from small metabolites and about 330 features from lipids. No statistical difference was observed between the two groups based on the feature numbers. Both small metabolite and lipid analysis with mass spectrometry showed outstanding dynamic range of about 5 magnitudes in small metabolite profiles, and about 4 magnitudes in lipid profiles. (FIGS. 11E-F).

An exemplary workflow for data analysis is shown in FIG. 13. The relative standard deviation (RSD) of each identified molecules was calculated in each group (GXP Positive, GXP negative). Molecules with less than about 30% RSD were used for t-test between GXP negative and GXP positive of each visit. Molecules showing statistical differences in all visits were used to generate ROC curves and for AUC (area under the curve) calculations. A feature ranking algorithm (SAM) was used to identify the significance of identified molecules. SAM was used to select features with the strongest discriminative power to distinguish two classes of samples in omics studies. In this study, SAM was adapted to visualize features that had the most powerful quantitative capacity to distinguish between non-TB subjects and TB infected subjects. Generally, SAM returned a list of features ranked by statistical powers, fold-change, and false-positive rate. Heat maps using Pearson correlation coefficient analysis of study subjects showed that molecular profiles may be used to segregate GXP positive and GXP negative groups. 347 small metabolites in the GXP negative group, and 325 small metabolites in GXP positive group, 217 lipids in the GXP negative group, and 198 lipids in the GXP positive group were selected for further analysis. Further, 22 molecules, including 13 metabolites and 9 lipid molecules were found to be statistically significant between GXP positive and GXP negative groups. Statistical analysis of microarrays (SAM) was applied to statistically significant features. The top 10 molecules that may be used to discriminate between GXP positive and negative groups comprised lipids PS 24:4, PI 18:4, Cer 8:0, DG O-8:0, PI 20:4 and metabolites NAM, Uridine, Kynurentine, PA and BA and were ranked using SAM algorithm as shown in FIG. 12A. Lipid nomenclature and molecular structure details related to the lipid biomarkers may be found by referring to several databases included the online LIPID MAPS database (Lipidomics Gateway). These results indicated that lipid molecules offered a better segregation between GXP positive and GXP negative subjects than metabolites. Lipid molecules showed a stronger correlation as well as ranked in the feature importance evaluation. This notion is further supported by the ROC curves and AUC calculation (FIG. 12B) as lipids alone contributed to about 93% segregation between GXP positive and negative subjects and adding metabolite markers only marginally improved scores.

It is challenging to interpret the origins of metabolites and lipids, for example, whether they originated from host-response or pathogen infection, until molecules specific to an organism type are identified. Lipid PS 24:4 showed the most segregation capability for active TB cases, and this molecule is present commonly in both human and Mtb. On the other hand, the metabolite NAM was detected at a much higher concentration in GXP positive subjects as NAM is a common precursor for peptidoglycan in bacterial walls.

The Abstract is provided to comply with 37 C.F.R. § 1.72(b), to allow the reader to determine quickly from a cursory inspection the nature and gist of the technical disclosure. It should not be used to interpret or limit the scope or meaning of the claims.

Although the present disclosure has been described in connection with the preferred form of practicing it, those of ordinary skill in the art will understand that many modifications can be made thereto without departing from the spirit of the present disclosure. Accordingly, it is not intended that the scope of the disclosure in any way be limited by the above description.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this disclosure is entitled. It should be understood that all actions may be expressed as a means for taking that action or as an element which causes that action. Similarly, each physical element disclosed should be understood to encompass a disclosure of the action which that physical element facilitates.

In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Further, the use of the transitional phrase "comprising" is used to maintain the "open-end" claims herein, according to traditional claim interpretation. Thus, unless the context requires otherwise, it should be understood that variations such as "comprises" or "comprising," are intended to imply the inclusion of a stated element or step or group of elements or steps, but not the exclusion of any other element or step or group of elements or steps. Such terms should be interpreted in their most expansive forms so as to afford the applicant the broadest coverage legally permissible.

REFERENCES

1. B. Bake, P. Larsson, G. Ljungkvist, E. Ljungström, and A-C Olin, "Exhaled particles and small airways," Respiratory Research (2019) 20:8.
2. Fennelly K. P., Martyny J. W., Fulton K. E., Orme I. M., Cave D. M., et al. (2004) Cough-generated aerosols of *Mycobacterium tuberculosis*: a new method to study infectiousness. Am J Respir Crit Care Med 169: 604-609.
3. Dina Hashoul and Hossam Haick, "Sensors for detecting pulmonary diseases from exhaled breath," Eur. Respir. Rev. 2019; 28: 190011.
4. Hunt, J., "Exhaled breath condensate: An evolving tool for noninvasive evaluation of lung disease," J. Allergy Clin. Immunol. 2002; 110:28-34.
5. Maria D. King, Andrew R. McFarland, "Bioaerosol Sampling with a Wetted Wall Cyclone: Cell Culturability and DNA Integrity of *Escherichia coli* Bacteria," Aerosol Sci. Technol., 46:82-93, 2012.
6. James J. McDevitt, Petros Koutrakis, Stephen T. Ferguson, Jack M. Wolfson, M. Patricia Fabian, Marco Martins, Jovan Pantelic, and Donald K. Milton, "Development and Performance Evaluation of an Exhaled-Breath Bioaerosol Collector for Influenza Virus," Aerosol Sci. Technol. 2013 Jan. 1; 47(4): 444-451.
7. Benjamin Patterson, Carl Morrow, Vinayak Singh, Atica Moosa, Melitta Gqada, Jeremy Woodward, Valerie Mizrahi, Wayne Bryden, Charles Call, Shwetak Patel, Digby Warner, Robin Wood, "Detection of *Mycobacterium tuberculosis* bacilli in bio-aerosols from untreated TB patients," Gates Open Research 2018, 1:11.
8. Wood R., Morrow C., Barry C. E., III, Bryden W. A., Call C. J., Hickey A. J., et al.: Real-Time Investigation of Tuberculosis Transmission: Developing the Respiratory Aerosol Sampling Chamber (RASC). PLoS One. 2016; 11(1): e0146658.
9. Rachel C. Wood, Angelique K. Luabeya, Kris M. Weigel, Alicia K. Wilbur, Lisa Jones-Engel, Mark Hatherill, and Gerard A. Cangelosi, "Detection of *Mycobacterium tuberculosis* DNA on the oral mucosa of tuberculosis patients," Sci. Rep. 5, 8668 (2015).
10. Fatima B. Wurie, Stephen D. Lawn, Helen Booth, Pam Sonnenberg, Andrew C. Hayward, "Bioaerosol production by patients with tuberculosis during normal tidal breathing: implications for transmission risk," Thorax 2016; 71: 549-554.

What is claimed is:

1. A system for diagnosing respiratory diseases in an individual using exhaled breath, the system comprising:
    a sample extraction component configured to receive an individual's face for extracting breath aerosol (EBA) particles expelled from the individual during a predetermined number of breath maneuvers into a flow of air fed into the sample extraction component;
    a sample capture component:
    fluidly connected to the sample extraction component and configured to collect the EBA particles into a collected liquid sample;
    a packed bed column disposed downstream of the sample capture component and configured to selectively capture the EBA particles from the collected liquid sample onto the packed bed;
    means to elute the collected EBA particles from the packed bed using one or more solvents; and
    a diagnostic device for analyzing the EBA particles in the one or more solvents.
2. The system of claim 1, wherein the EBA particles comprises at least one of microbes, virus, metabolite biomarkers, lipid biomarkers, and proteomic biomarkers characteristic of the respiratory disease.
3. The system of claim 1, wherein the flow rate of air fed into the sample capture component is between about 50 L/min and about 500 L/min.
4. The system of claim 1, wherein the volume of the collected liquid sample is between about 100 microliter and about 10 ml.
5. The system of claim 1, further comprising an air pump and an impactor, wherein the air pump provides the flow of air to carry the exhaled breath from the extraction component into the impactor and, wherein the impactor separates the EBA particles from exhaled breath to produce the collected liquid sample.
6. The system of claim 5, wherein the impactor comprises at least one of a cyclone, a wetted wall cyclone, one or more wetted film impactors, a virtual impactor, and an impinger.
7. The system of claim 1, wherein the sample extraction component comprises at least one of a cone shaped device, a shroud, CPR rescue mask, a CPAP mask, a ventilator mask, and a medical universal mouthpiece.
8. The system of claim 1, wherein the diagnostic device comprises at least one of PCR, rt-PCR, immuno-based assay, mass spectrometer (MS), MALDI-MS, ESI-MS, GC-MS, GC-IMS and MALDI-TOFMS.
9. The system of claim 1, further comprising one or more chilling devices configured to be in thermal communication with the sample capture component.
10. The system of claim 9, wherein the sample capture component is chilled to a temperature greater than about 0° C. and less than about 10° C. using the one or more chilling devices.

11. The system of claim 9, wherein the sample capture component is chilled to a temperature greater than about 0° C. and less than about 4° C. using the one or more chilling devices.

12. The system of claim 1, further comprising one or more sensors configured be in fluid communication with the sample extraction component, wherein the output of the one or more sensors is used to calculate the total cumulative volume of exhaled breath aerosol particles entering the sample capture component.

13. The system of claim 12, wherein the one or more sensors comprises at least one of a $CO_2$ sensor, an oxygen sensor, a humidity sensor, an optical particle size counter, an aerodynamic particle sizer, and a nephelometer.

14. The system of claim 1, wherein the collected liquid sample is transferred to the packed bed column using at least one of a dispensing pump and a robotic sample transfer system.

15. The system of claim 2, wherein the lipid biomarkers comprise biomarkers characteristic of *Mtb*.

16. The system of claim 1, wherein the packed bed column comprises solid particles comprising at least one of resins, cellulose, silica, agarose, and hydrated $Fe_3O_4$ nanoparticles.

17. The system of claim 1, wherein the packed bed column comprises resin beads having C18 functional groups on the surface.

18. The system of claim 17, wherein the resin beads have a nominal diameter of between about 12 μm and about 20 μm.

19. The system of claim 17, wherein the weight of the packed bed is about 25 mg.

20. The system of claim 1, wherein the means to elute the collected EBA particles from the packed bed using one or more solvents comprises at least one of one or more syringes, and one or more pumps to flush the packed bed with the one or more solvents.

21. The system of claim 1, wherein the one or more solvents comprises at least one of acetonitrile, methanol, acid, isopropanol, the remaining being water.

22. A method for diagnosing respiratory diseases in an individual using exhaled breath, the method comprising:
extracting EBA particles expelled into a flow of air fed into a sample extraction component configured to receive an individual's face;
collecting the EBA particles from exhaled breath and air as a collected liquid sample using a sample capture component;
capturing the EBA particles in the collected liquid sample using a packed bed column disposed downstream of the sample capture component to selectively capture the EBA particles from the collected liquid sample onto the packed bed;
eluting the collected EBA particles from the packed bed using one or more solvents; and
analyzing the EBA particles comprised in the one or more solvents.

23. The method of claim 22, wherein the one or more solvents comprises at least one of acetonitrile, methanol, acid, isopropanol, the remaining being water.

24. The method of claim 22, wherein the one or more solvents comprises between about 50 vol.-% and about 70 vol.-% acetonitrile in water.

25. The method of claim 22, wherein the one or more solvents comprises between about 50 vol.-% and about 70 vol.-% isopropanol in water.

26. The method of claim 22, wherein the eluting step comprises washing the packed bed column with about 50 vol.-% ACN in a first step and with about 70 vol.-% IPA in a second step.

27. The method of claim 22, wherein the analysis step further comprises detecting at least one of lipid biomarkers PS 24:4, PI 18:4, Cer 8:0, DG O-8:0, and PI 20:4 to determine the presence or absence of a respiratory disease.

* * * * *